(12) United States Patent
Curran et al.

(10) Patent No.: US 6,749,756 B1
(45) Date of Patent: Jun. 15, 2004

(54) REACTION AND SEPARATION METHODS

(75) Inventors: Dennis P. Curran, Pittsburgh, PA (US); Oscar de Frutos Garcia, Madrid (ES); Yoji Oderaotoshi, Fukuoka (JP)

(73) Assignee: University of Pittsburgh, Pittsburgh, PA (US)

( * ) Notice: Subject to any disclaimer, the term of this patent is extended or adjusted under 35 U.S.C. 154(b) by 0 days.

(21) Appl. No.: 09/506,779

(22) Filed: Feb. 18, 2000

(51) Int. Cl.[7] .................. B01D 15/08; C02F 1/28; G01N 33/53; G01N 33/543; C07C 25/13
(52) U.S. Cl. ............... 210/668; 435/DIG. 2; 435/DIG. 14; 435/DIG. 15; 435/DIG. 16; 435/DIG. 17; 435/DIG. 18; 435/DIG. 19; 435/DIG. 46; 435/DIG. 48; 435/DIG. 49; 435/DIG. 50; 435/7.1; 435/7.2; 436/501; 436/518; 530/333; 530/334; 530/344; 530/345; 210/656; 210/658; 210/739; 210/749; 210/763; 570/123; 570/124
(58) Field of Search ............... 435/DIG. 2, 14–19, 435/46, 48–50, 7.1, 7.2; 436/501, 518; 530/333, 334, 344, 345; 210/656, 658, 668, 739, 749, 763; 570/123, 124

(56) References Cited

U.S. PATENT DOCUMENTS

| | | | |
|---|---|---|---|
| 4,454,233 A | | 6/1984 | Wang |
| 5,340,453 A | | 8/1994 | Jackson |
| 5,401,847 A | | 3/1995 | Glazer |
| 5,463,082 A | | 10/1995 | Horvath |
| 5,565,324 A | * | 10/1996 | Still et al. ............... 435/6 |
| 5,604,097 A | * | 2/1997 | Brenner ............... 435/6 |
| 5,777,121 A | | 7/1998 | Curran |
| 5,798,032 A | | 8/1998 | Khan |
| 5,859,247 A | * | 1/1999 | Curran ............... 546/2 |
| 6,156,896 A | | 12/2000 | Curran |
| 6,168,913 B1 | * | 1/2001 | Hochlowski et al. ............... 435/4 |

FOREIGN PATENT DOCUMENTS

WO  WO 01/61332  2/2000

OTHER PUBLICATIONS

Bergbreiter, D.E.: Zhang, L. Separation of Enantiomers as Differentially Sized Pseudoenantiomeric Salts. J. Chem. Soc. Chem. Comm. 1993, 596–597.

Curran, D.P.; Halida, S.; He, M. Thermal Allylations of Aldehydes with a Fluorous Allylstannane. Separation of Organic and Fluorous Products by Solid Phase Extraction with Fluorous Reverse Phase Silica Gel. J. Org. Chem. 1997, 62, 6714–6715.

Curran, D.P.; Luo, Z. Y. Fluorous Synthesis with Fewer Fluorines (Light Fluorous Synthesis): Separation of Tagged from Untagged prodcuts by Solid–Phase Extraction with Fluorous Reverse–Phase Silica gel. J. Am. Chem. Soc. 1999, 121, 9069–9072.

Curran, D. P. Strategy–Level Separations in Organic Synthesis: from Planning to practice, Angew. Chem., Int. ed. Eng. 1998, 37, 1175–1196.

(List continued on next page.)

Primary Examiner—Maurie Garcia Baker
(74) Attorney, Agent, or Firm—Bartony & Hare, LLP

(57) ABSTRACT

A method of separating compounds that includes the steps of: tagging at least a first organic compound with a first tagging moiety to result in a first tagged compound; tagging at least a second organic compound with a second tagging moiety different from the first tagging moiety to result in a second tagged compound; and separating the first tagged compound from a mixture including the second tagged compound using a separation technique based upon differences between the first tagging moiety and the second tagging moiety. The present invention also provides a method for carrying out a chemical reaction including the steps of: tagging a plurality of compounds with different tagging moieties to create tagged compounds, conducting at least one chemical reaction on a mixture of the tagged compounds to produce a mixture of tagged products, and separating the mixture of tagged products by a separation technique based upon differences in the tagging moieties.

11 Claims, 6 Drawing Sheets

A general mixture synthesis with fluorous tags using a mixture of tagged compounds.

S = substrate
F = fluorous tag
P = product

OTHER PUBLICATIONS

Danielson, N. D.; et al. Fluoropolymers and Fluorocarbon Bonded Phases as Column Packings for Liquid Chromatography. J. Chromat. 1991, 544, 187–199.

Gravert, D. J.; et al. Organic Synthesis on Soluble Polymer Supports; Liquid–Phase Methodologies, Chem. rev. 1997, 97, 489–509.

Griffey, R. H. ; et al. rapid Deconvolution of Combinatorial Libraries Using HPLC Fractionation. Tetrahedron 1998, 54, 4067–4076.

Houghten, R. A.; et al. Mixture–Based Synthetic Combinatorial Libraries. J. Med. Chem. 1999, 42, 3743–3778.

Josien, H.; Curran, D. P. Synthesis of (S)–Mappicine and Mappicine Ketone Via Radical Cascade reaction of Isonitriles. tetrahedron 1997, 53, 8881–8886.

Kainz, S.; Luo, Z. Y.; Curran, D. P. et al. Synthesis of Perfluoroalkyl–Substituted Aryl Bromides and Their Purification over Fluorous Reverse Phase Silica, Synthesis 1998, 1425–1427.

Lam, K. S.; Lebl, M.; et al. The "One–Bead–One–Compound" Combinatorial Library Method. Chem. Rev. 1997, 97, 411–448.

Thompson, L. A.; Ellman, J. A. Synthesis and applications of small molecule libraries Chem. Rev. 1996, 96, 555–600.

Vedejs, E.; Chen, C. Parallel kinetic resolution. J. Am. Chem. Soc. 1997, 119, 2584–2585.

* cited by examiner

Figure 1a. A general mixture synthesis with fluorous tags using a mixture of tagged compounds.
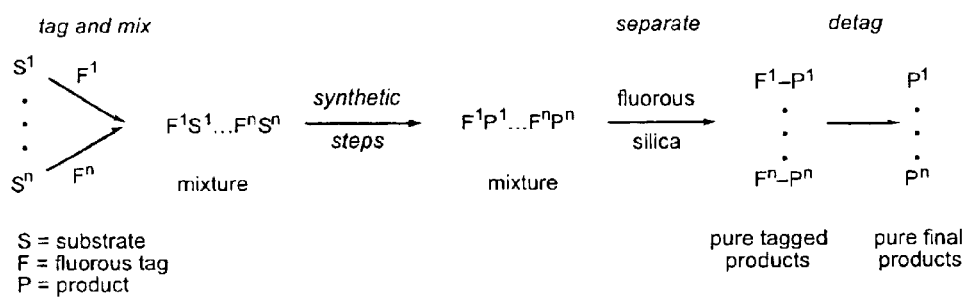
S = substrate
F = fluorous tag
P = product
Figure 1b. A general mixture synthesis with fluorous tags using a mixture of tagged compounds and a mixture of reactants.
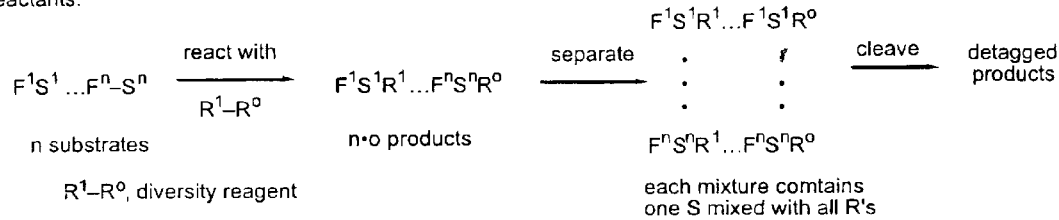
Figure 1c. A general mixture synthesis with fluorous tags using fluorous tagged reactants and a substrate.
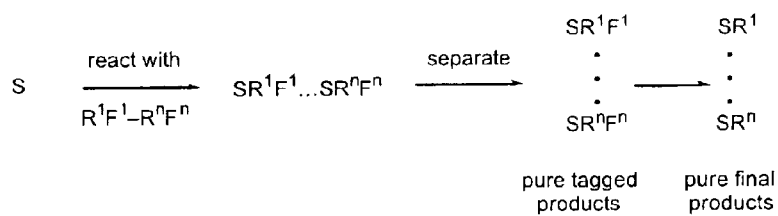

Figure 2. A representative example of a synthesis with a mixture of flourous tagged compounds and a mixture of reactants

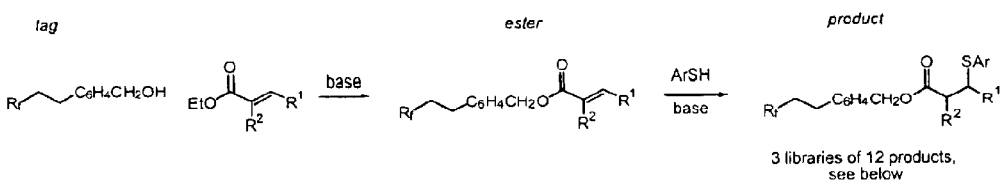

3 libraries of 12 products, see below

| Tags | Esters | Thiols |
|---|---|---|
| $R^f$ | $R^1$ $R^2$ | |
| x $C_6F_{13}$ | 1 Me H | a $C_6H_5$ |
| y $C_8F_{17}$ | 2 Pr H | b 2-naphthyl |
| z $C_{10}F_{21}$ | 3 H Me | c p-MeOC$_6$H$_4$ |
| | | d p-$^t$BuC$_6$H$_4$ |

| Library | Esters | Products in order of retention times (min) on Fluofix column |
|---|---|---|
| 1 | 1x, 2y, 3z | 1xc (18.5); 1xb (18.9); 1xa (19.3); 1xd (23.8); 2yc (28.7); 2yb (28.7); 2ya (29.5); 2yd (32.6); 3zc (34.1); 3zb (34.1); 3za (35.1); 3zd (37.9) |
| 2 | 1y, 2z, 3x | 3xc (18.1); 3xb (18.5); 3xa (18.7); 3xd (23.4); 1yc (27.0); 1yb (27.0); 1yc (27.6); 1yd (31.2); 2zc (35.6); 2zb (35.6); 2za (36.5); 2zd (38.8) |
| 3 | 1z, 2x, 3y | 2xc (20.4); 2xb (20.9); 2xa (21.0); 2xd (25.3); 3yc (26.4); 3yb (26.4); 3ya (27.0); 3yd (30.8); 1zc (34.2); 1zb (34.2); 1za (35.1); 1zd (37.8) |

Figure 3. A representative HPLC trace of a library of compounds produced in the synthesis of Figure 2.[a]
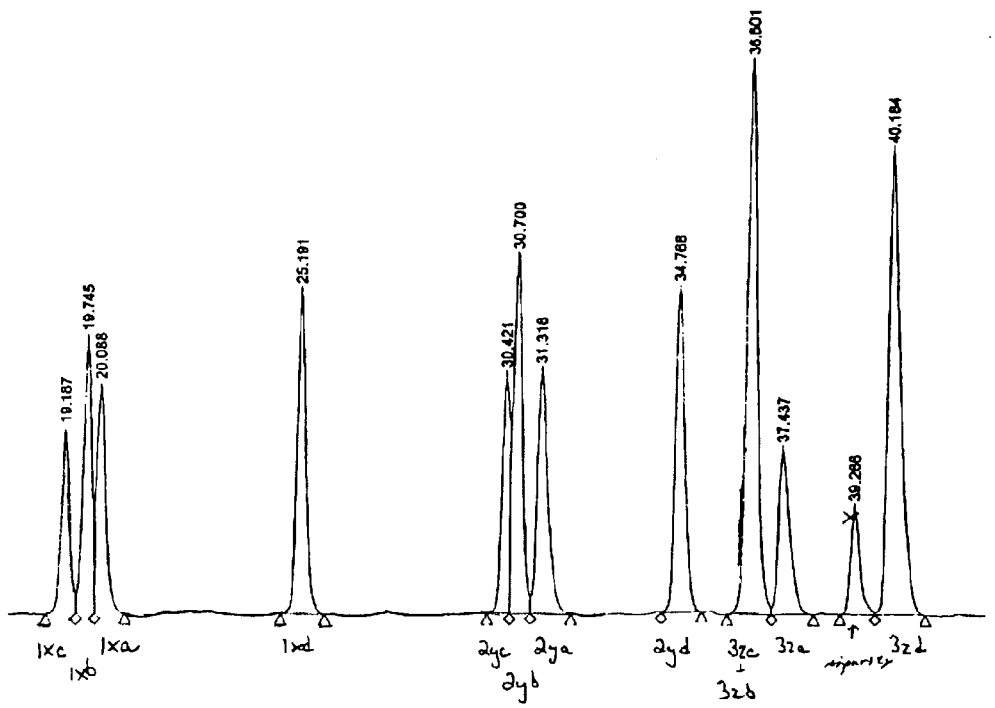
a) Retention times are listed in minutes; compound numbers refer to Figure 2; Fluofix column eluting with a gradient of 80% methanol/water increased to 100% methanol over 40 min. The peak at 39 min is an unknown impurity.

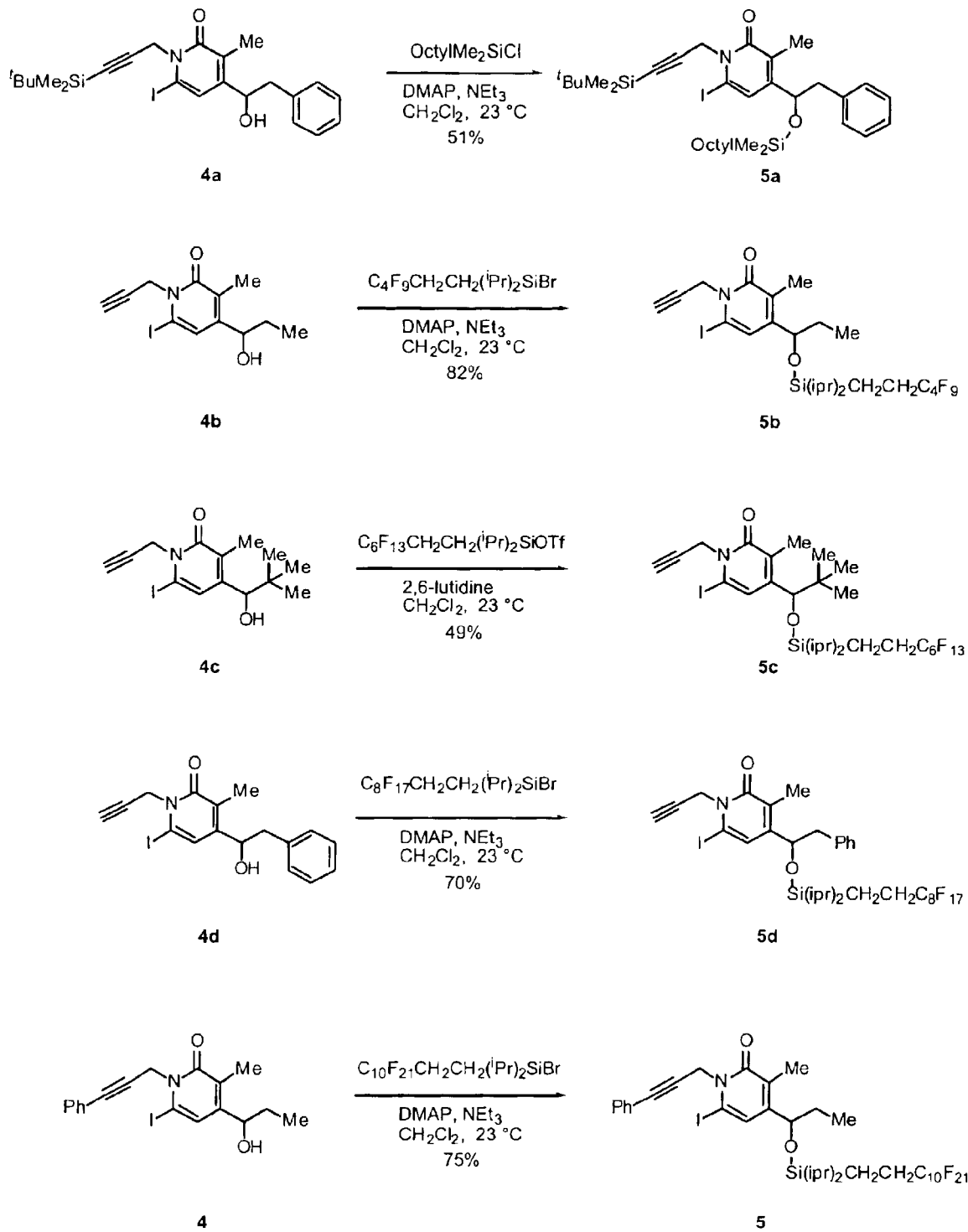
Figure 4. Preparation of Precursors for a Mixture Synthesis of Mappicine Analogs

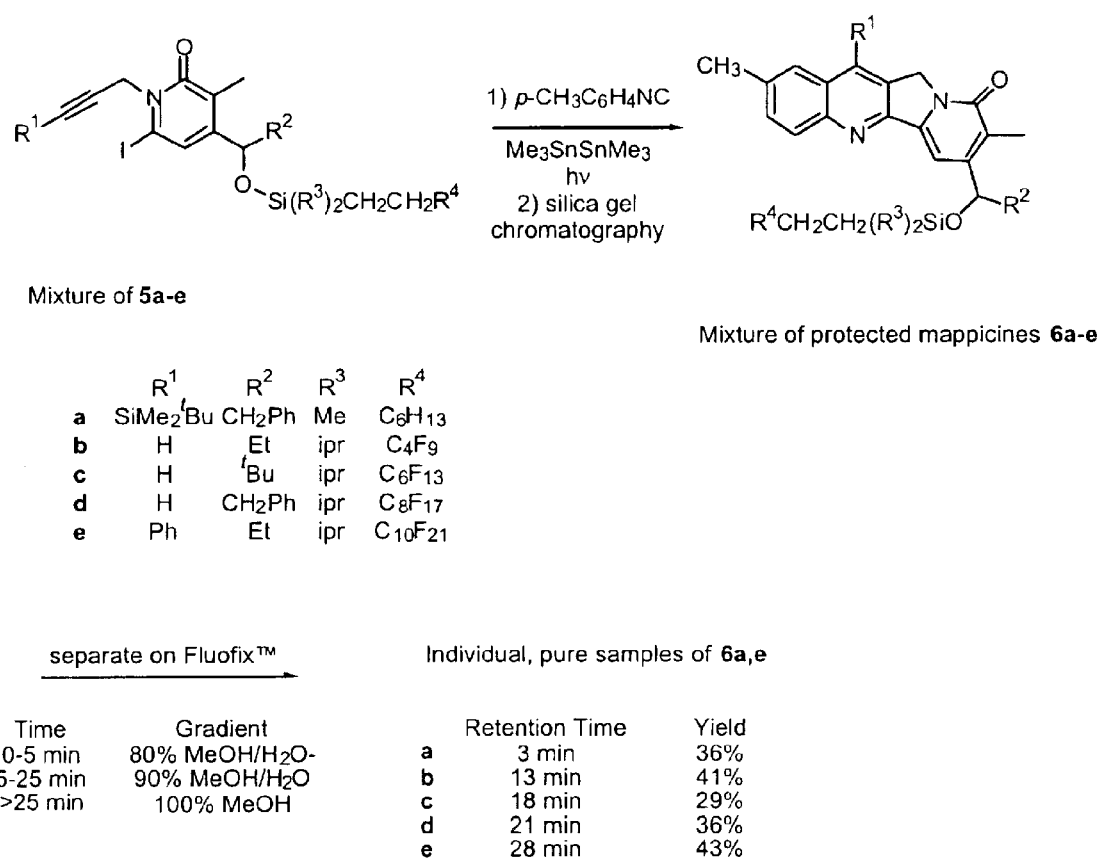
Figure 5. Mappicine Mixture Synthesis and Separation

Figure 6. Preparation of precursors for a mixture synthesis of mappicine analogs (Example 8)
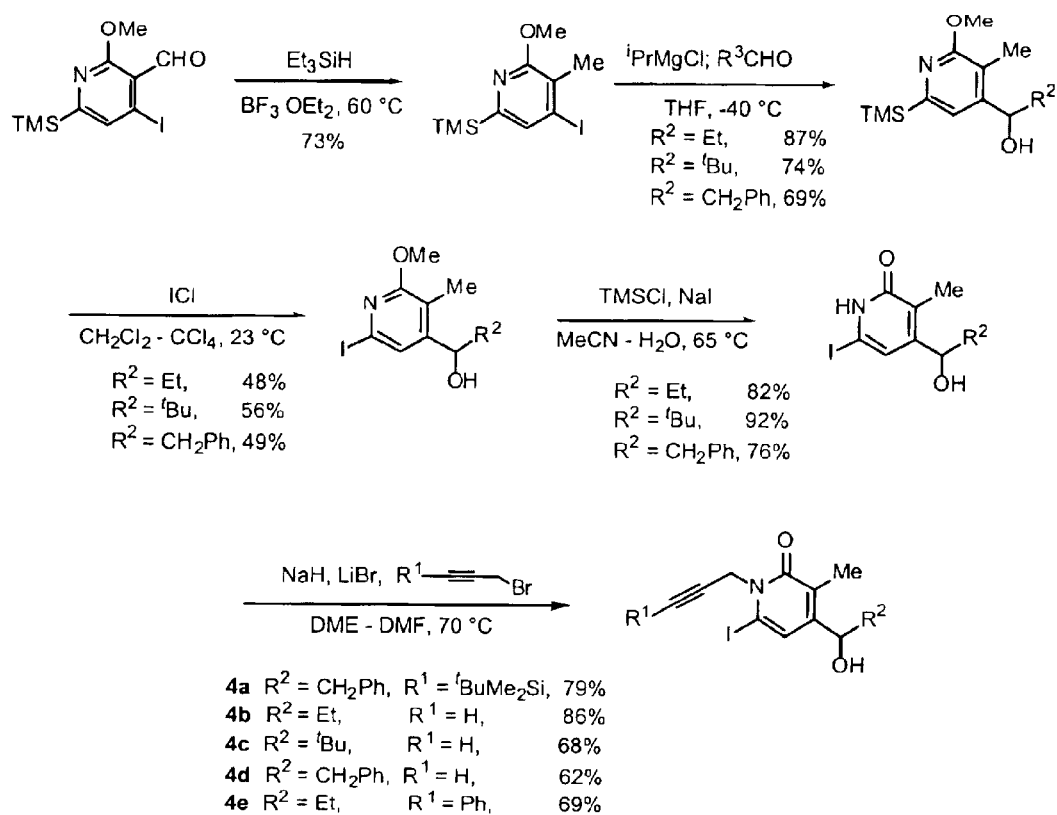

REACTION AND SEPARATION METHODS

GOVERNMENT INTERESTS

This invention was made with government support under grant number Grant No. GM33372 awarded by the National Institutes of Health. The government has certain rights in this invention.

FIELD OF THE INVENTION

The present invention relates to methods of carrying out reactions and separations, and, especially, to reactions and separations involving tagging.

BACKGROUND OF THE INVENTION

Interest in expediting the synthesis of organic compounds for use as potential drugs, agricultural agents, catalysts, ligands and other uses has led to the development of a number of methods for synthesis that use "mixtures" of organic compounds rather than pure organic compounds. Simple mathematics demonstrates the potential power of mixture synthesis. For example, to execute a parallel (or sequential) n-step synthesis starting from m different starting materials requires n·m individual reactions with all the attendant equipment (for example, reaction vessels) and manipulations (transfers, workups, chromatography, etc). However, if the m compounds are mixed at the beginning, and then carried through the n-step synthesis and separated, only n separate steps are required.

The value of mixture synthesis has recently been demonstrated in the area of solid phase synthesis with techniques of split synthesis. For example, by using "one bead/one compound" techniques, large libraries of compounds can be made in relatively few steps. See, for example, Lam, K. S., et al., "The 'One-Bead-One-Compound' Combinatorial Library Method," *Chem. Rev.*, 96, 411–488 (1996); Thompson, L. A. and Ellman, J. A., "Synthesis and Applications of Small Molecule Libraries," *Chem. Rev.*, 96, 555–600 (1996). Each bead is effectively a kind of reaction vessel that permanently holds its "contents" (substrates and their products) by chemical bonds. The beads are mixed, not the compounds. Likewise, methods such as using "tea bags", "microkans", and other physical equipment have been introduced to facilitate mixture synthesis. However, in all those solid phase synthesis techniques it is the container of the supported substrates that is mixed. The substrates themselves are polymer-bound and are not mixed. Such solid phase synthesis techniques are typically limited by difficulty in developing suitable reaction conditions for generally biphasic reactions.

Organized mixtures of organic molecules (libraries) have also been generated by using solution phase chemistry. See, for example, Houghten, R. A., "Mixture-Based Synthetic Combinatorial Libraries," *J. Med. Chem.*, 42, 3743–3778 (1999). Although such libraries can be made in different ways, a common thread in that approach is that no effort is made to separate the mixture into individual pure components. Instead, libraries and sub-libraries are constructed and assays are conducted such that an active component (or components) can be identified by a process of deconvolution. Deconvolution processes are generally methods which attempt to identify the most active members of a library of compounds without isolating the individual components of the library. In general, mixtures of compounds are tested to measure an average activity of the mixture. Mixtures can be separated by HPLC fractionation or other standard techniques for separation of organic molecules, but the separation typically does not provide pure components since mixture components overlap. See, for example, Griffey, H. Y., "Rapid Deconvolution of Combinatorial Libraries Using HPLC Fractionation," *Tetrahedron*, 54, 4067–4076 (1998). Further, the outcome of the separation (that is, which fractions are pure and which are mixtures, as well as which fraction contains which compound(s)) is not generally known in advance.

It is very desirable to develop improved reaction and separation systems to, for example, enhance the utility of mixture synthesis.

SUMMARY OF THE INVENTION

In general, the present invention provides a method of separating compounds that includes the steps of: tagging a first organic compound with a first tagging moiety to result in a first tagged compound; tagging at least a second organic compound with a second tagging moiety different from the first tagging moiety to result in a second tagged compound; and separating the first tagged compound from a mixture including the second tagged compound using a separation technique based upon differences between the first tagging moiety and the second tagging moiety. Preferably, the separation technique is based upon difference in the fluorous nature of the first tagged compound and the second tagged compound, differences in total charge between the first tagged compound and the second tagged compound, differences in size between the first tagged compound and the second tagged compound, and/or differences in polarity between the first tagged compound and the second tagged compound.

As used herein, the term "tagging" refers generally to attaching a moiety or group (referred to as a "tagging moiety" or "tagging group") to a compound to create a "tagged compound". Preferably, the tagging moiety is attached via covalent bond. However, other strong attachments such as ionic bonding or chelation can also be used. In the present invention, different tagging moieties are preferably used on different compounds to facilitate separation of such tagged compounds.

For example, the tagging moieties can be fluorous moieties that differ in fluorine nature (for example, fluorine content and/or structure). As used herein, the term "fluorous", when used in connection with an organic (carbon-containing) molecule, moiety or group, refers generally to an organic molecule, moiety or group having a domain or a portion thereof rich in carbon-fluorine bonds (for example, fluorocarbons, fluorohydrocarbons, fluorinated ethers and fluorinated amines). The term "fluorous substrate," thus refers generally to a substrate comprising a portion rich in carbon-fluorine bonds. As used herein, the term "perfluorocarbons" refers generally to organic compounds in which all hydrogen atoms bonded to carbon atoms have been replaced by fluorine atoms. The terms "fluorohydrocarbons" and "hydrofluorocarbons" include organic compounds in which at least one hydrogen atom bonded to a carbon atom has been replaced by a fluorine atom. The attachment of fluorous moieties to organic compounds is discussed in U.S. Pat. Nos. 5,859,247 and 5,777,121, the disclosures of which are incorporated herein by reference.

Separation of the tagged compounds of the present invention is achieved by using separation techniques that are complementary to (based upon differences between) the tagging moieties. For example, in the case that compounds are tagged with fluorous moieties that differ in fluorine content, the tagged compounds may be separated using a fluorous separation technique (for example, fluorous reverse phase chromatography).

As used herein, the term "fluorous separation technique" refers generally to a method that is used to separate mixtures containing fluorous molecules or organic molecules bearing fluorous domains or tags from each other based predominantly on the fluorous nature of molecules (for example, size and/or structure of the fluorous molecule or domain). Fluorous separation techniques include but are not limited chromatography over solid fluorous phases such as fluorocarbon bonded phases or fluorinated polymers. See, for example, Danielson, N. D. et al., "Fluoropolymers and Fluorocarbon Bonded Phases as Column Packings for Liquid Chromatography," *J. Chromat.*, 544, 187–199 (1991). Examples of suitable fluorocarbon bonded phases include commercial Fluofix® and Fluophase™ columns available from Keystone Scientific, Inc. (Bellefonte, Pa.), and FluoroSep™-RP-Octyl from ES Industries (Berlin, N.J.). Other fluorous separation techniques include liquid-liquid based separation methods such as countercurrent distribution with a fluorous solvent and an organic solvent.

As indicated above, a number of tagging strategies other than fluorous tagging are suitable for use in the present invention. In general, any tagging strategy that facilitates separation of the tagged compounds based on differences in the tag is suitable. If compounds that are tagged are to undergo one or more reactions to produce tagged product compounds that are to be separated, the tagging moieties preferably do not substantially interfere with the reaction(s) and are not cleaved during the reaction(s). In that regard, the product compounds must be tagged to achieve separation based upon differences in the tagging moiety. As will be discussed further below, the manner/order of steps in which the tagged product compounds become tagged is unimportant.

In addition to tagging moieties that differ in fluorine content, tagging moieties that, for example, differ in total charge can also be used in the present invention. Such tagged compound can, for example, be separated by electrophoresis. The tagging moieties can also be oligomers, polymers, or dendrimers that differ in size. In the case that the tagging moieties are oligimers, polymers or dendrimers, the tagged compounds can, for example, be separated by size exclusion chromatography. As used herein, the terms, "oligomers" and "polymers" refer generally to molecules that are made by linking together repeating units of one or more small molecules called monomers. Generally, oligomers include fewer monomer units than polymers, although the precise border between an oligomer and a polymer in not well defined. In the present invention, so-called "soluble" oligomers and polymers are preferred. Soluble polymers are discussed in, for example, Gravert, D. J. and Janda, K. D., "Organic Synthes is on Soluble Polymer Supports: Liquid-phase Methodologies," *Chem. Rev.*, 97, 489–509 (1997). Through use of soluble oligimer or polymer tags, substrates or products can be attached to oligomer or polymer tags of different molecular weights or molecular weight ranges and then the tagged substrates can be mixed to generate a true mixture which can, if desired, be reacted in standard solution phase organic reactions prior to separation. An example of a suitable family of oligomer/polymer tags is polyethylene glycol (PEG, $H(OCH_2CH_2)_nOH$). PEG is soluble in an assortment of organic solvents, has two terminal hydroxyl groups for attachment/detachment of compounds and products, and can be purchased in a range of sizes (for example, average molecular weights of 1,000, 1,500, 2,000, 4,600, etc).

As used herein, the term "dendrimer" refers generally to branched or hyperbranched molecules that are synthesized in generations by attachments of successive sets of building blocks to a core (or the inverse). See, for example, Dendrimers, F. Vogtle, Ed., Springer-Verlag Berlin: Heidelberger Platz 3/W-1000 Berlin 33/Germany, 1–18 (1998). Unlike traditional oligomers and polymers, dendrimers can be made largely as pure molecules each bearing the same number of building blocks. To the contrary, oligomers and polymers are generally available only as mixtures of molecules with a distribution of sizes centered around an average. Different generations of dendrimers make convenient families of tags. For example, the various generations of the commercially available "DAB" polypropylene amine dendrimers (tetraamine, octaamine, hexadecamine, etc.) vary widely in size and molecular weight and provide increasing numbers of amines for attachment. Starburst® (PAMAM) dendrimers provide another example of a family of dendrimers tags.

The tagging moieties can also differ in polarity, in which case the tagged compounds can, for example, be separated by standard or, preferably, reverse phase chromatography.

The present invention also provides a method for carrying out a chemical reaction including the steps of: tagging a plurality of compounds with different tagging moieties to create tagged compounds, conducting at least one chemical reaction on the tagged compounds to produce a mixture of tagged products, and separating the mixture of tagged products by a separation technique based upon differences in the tagging moieties. The method may further include the step of removing the tagging moieties from the tagged products after separation. The tagging moieties are removable using standard reactions as known in the art. The tagging strategies described above can be used.

The order or sequence of steps in which the tagged products are produced is unimportant. In one embodiment of the present invention, for example, compounds are tagged and then mixed. In other embodiments, the tagging step itself generates the tagged compound mixture. In still other embodiments, the compounds are already mixed prior to the tagging. In these embodiments, each tag is preferably attached to a single compound by using selective reactions known to those skilled in the art. In general, selective reactions are those in which one component or subset of components of a mixture reacts faster than another component or subset of components. Selective reactions can, for example, be based on differences in reacting functional groups, steric effects, electronic effects, and stereoelectronic effects, among other things. For example, if a mixture contains a secondary and a primary alcohol, it is possible to use the higher reactivity of the primary alcohol to selectively attached a first tag to it, and then attach a second tag to the remaining secondary alcohol. If a mixture contains two enantiomers, it is possible to selectively tag one enantiomer with a first tag using a chiral catalyst or reagent, and then tag the remaining enantiomer with a second tag. In these types of reactions, it is preferable that each tagging reaction be selective for its target component(s) of the mixture to a level of at least approximately 80%. More preferably, the level of selectivity is at least approximately 90%.

The present invention is particularly useful in conjunction with mixture synthesis or combinatorial synthesis. It is thus beneficial to briefly discuss a number of terms commonly used in such synthetic schemes. As used herein, the term "substrate" refers generally to a reaction component that is a starting material of a synthetic reaction, normally purchased prepared in a prior step. The terms "product" or "target product" refer generally to the target or desired molecule(s) of a transformation derived by reaction of the substrate with the other reaction component(s) in a reaction medium. The terms "side product" or "byproduct" refer generally to a product derived from any component(s) of the reaction medium which is not the target product and is preferably separated therefrom.

The term "reagent," as used herein refers generally to a chemical entity that is required for a reaction but contributes either an invariant piece or no piece to the products of a mixture synthesis or a combinatorial synthesis. The term "reactant," as used herein refers generally to a type of molecule that contributes a variable piece to the products of a mixture synthesis or a combinatorial synthesis. The distinction between the terms "reactant" and "reagent" in "common" (non-mixture and non-combinatorial) organic syntheses is vague, but those skilled in the art often refer to a reaction component as a reagent if it contributes no piece, a rather small piece, or a piece without carbon atoms therein to the target product. As used herein, the term "reagent" includes a catalyst if used in a substoichiometric quantity. Both substrates and reactants are sometimes referred to as starting materials or starting compounds.

In common organic synthesis, individual steps are conducted sequentially until the final target molecule or product is made. In combinatorial organic synthesis, the target is not a single molecule but instead a "library" of several to millions of molecules. Combinatorial synthesis can be carried out by parallel synthesis of individual pure compounds or synthesis of mixtures.

Once again, the manner in which a product compound is tagged in a mixture synthesis or combinatorial synthesis in the present invention is unimportant. For example, a tagging moiety can be incorporated into a substrate, reactant and/or reagent to create a tagged product.

Likewise, individual or mixed, untagged product compounds can be directly tagged with tagging moieties to create tagged product compounds. It is important that the different products or subsets of products have different tags.

In mixture and combinatorial synthesis, multiple reactions are conducted either together or in parallel to provide multiple products. In mixture synthesis and combinatorial synthesis, the premium of simple methods of purification is even higher than in normal synthesis. For this reason, combinatorial synthesis is now commonly conducted on the solid phase, where purification can be effected simply by filtration. However, conducting such reactions can be difficult because the solid-bound reaction component never truly dissolves in the reaction solvent.

There are a number of advantages afforded by carrying out mixture or combinatorial synthesis in a liquid phase as enabled by the present invention. For example, many reactions are preferably conducted in a homogenous liquid phase. This is in direct contrast to solid phase syntheses, where true homogeneity is never obtained.

Moreover, unlike deconvolution methods, the methods of the present invention can be used to readily provide pure product compounds for testing. In the case of deconvolution methods, mixtures of product compounds are tested to identify the highest average activity. Much valuable information can be lost in such deconvolution methods. For example, even testing of non-optimal (with respect to biological activity, for example) pure compounds provides valuable information.

Furthermore, unlike standard separation techniques, the separation of a mixture of tagged compounds in the present invention is determined primarily by the nature of the tag rather than the component/compound that is tagged. Preferably, the tagging compounds of the present invention are chosen such that they are separable in a predetermined manner via a complementary separation technique. For example, compounds of different fluorine content will separate in a predetermined order during chromatography over solid fluorous phases. Because compounds are preferably selectively tagged with certain tagging moieties in the present invention, the manner (for example, order) in which specific tagged compounds will separate is predetermined, thereby potentially eliminating the need to chemically identify the results of the separation.

In general, the present invention provides substantially universal methods for synthesizing and separating organic compounds. The methods are particularly useful in mixture and combinatorial synthesis techniques, but find use in substantially any reaction and/or separation requiring separation of one organic compound from another organic compound.

Typically, known standard (non-tagged) reactions can be carried out under the present invention with one or more tagged compounds within the range of reaction conditions used in the corresponding standard (non-tagged) reactions. The present invention is equally applicable, however, to newly developed organic reactions.

Transformations under the method of the present invention thus generally parallel the transformations of known "non-tagged" substrates with the advantages that the tagged products are more easily separated from untagged reaction components and from each other.

BRIEF DESCRIPTION OF THE DRAWINGS

FIG. 1a illustrates a general mixture synthesis with fluorous tags using a mixture of tagged compounds.

FIG. 1b illustrates a general mixture synthesis with fluorous tags using a mixture of tagged compounds and a mixture of reactants.

FIG. 1c illustrates a general mixture synthesis with fluorous tags using fluorous tagged reactants and a substrate.

FIG. 2 illustrates a representative example of a synthesis with a mixture of flourous tagged compounds and a mixture of reactants.

FIG. 3 illustrates a representative HPLC trace of a library of compounds produced in the synthesis of FIG. 2.

FIG. 4 illustrates preparation of precursors for a mixture synthesis of mappicine analogs.

FIG. 5 illustrates mappacine mixture synthesis and separation.

FIG. 6 illustrates synthesis of tagged compounds for a mappacine mixture synthesis.

DETAILED DESCRIPTION OF THE INVENTION

The present invention provides methods for the synthesis and/or separation of mixtures of organic compounds based on a tagging strategy. The methods allows the final mixture to be separated into components in an organized fashion based on the tag. The invention is especially useful as an alternative to the traditional methods of organic synthesis in which a single compound is taken through a series of reactions and purifications one step at a time to make a single product. The invention is broadly applicable to many types of reactions and reaction conditions with the full range of organic compounds and products, including but not limited to, carbocycles, heterocycles, acyclic molecules, aromatic molecules, peptides, carbohydrates and so on. The methods of the present invention can be used, for example, to make an organic compounds such as a natural product and its enantiomer and/or other stereoisomers through a sequence of chemical reactions followed by separation. It can also be used to make a series of compounds bearing different substituents.

In several embodiments, the methods of the present invention are applied in the synthesis of mixture and/or combinatorial libraries by manual or automated methods. By multiplying the number of compounds to be synthesized with only a small amount of additional effort, the present invention expedites both traditional synthesis and combinatorial library synthesis.

In one embodiment, the present invention provides a method of tagging at least two organic compounds with one among a family of tags designed to control separation at a later stage. Each compound (or mixture of compounds) is tagged with a different tag. The tagged compounds are then combined to generate a mixture, which is processed through one or more chemical reactions to form a mixture of tagged products. The mixture of tagged products is then separated into fractions by a separation method that complements the tag. In other words, the separation of the mixture is determined primarily by the nature of the tag rather than the component that is tagged.

In another embodiment, a series of tagged starting compounds are added individually or as a mixture to one or more tagged or untagged compounds to produce a mixture of tagged products. After removal of the tags, the untagged products are chemically different from the untagged starting compounds.

The tags are generally organic compounds that contain a suitable site of attachment, such as but not limited to, a hydroxyl group, an amino group, a silyl group, an alkyl group or an acyl group, to which an organic substrate is attached through a covalent chemical bond. Tags may have attached thereto a single compound or they may have attached thereto multiple copies of the same or different compounds that are preferably attached and detached in substantially the same way. Likewise, a single substrate may have attached thereto a single or multiple tagging moieties. As used herein, a "family" of tags is a series of similar molecules that differs in some "regular" or predetermined fashion to allow for the separation of tagged products based on the nature of the tag. In one embodiment, the predetermined difference between tags is "incremental." For example, members of a family can be charged tags that differ by one (or two, or more) negative or positive charges. Members of a family can be dendrimers that vary by generation (second generation, third generation, etc.). Members of a family can be oligomers or soluble polymers that differ in size. Members of a family can be linear hydrocarbons that differ in chain length. Members of a family of fluorous tags can vary in the number of fluorines, and so on. It is not necessary that the increment of variation be constant. Nor is it necessary that the variation between members of a family of tags be incremental provided that the variation is sufficiently different to control the separation of the tagged compounds.

Members of an example of an incremental family of is fluorous tags include: —Si(Me)$_2$CH$_2$CH$_2$C$_4$F$_9$, —Si(Me)$_2$CH$_2$CH$_2$C$_5$F$_{11}$, —Si (Me)$_2$CH$_2$CH$_2$C$_6$F$_{13}$, —Si(Me)$_2$CH$_2$CH$_2$C$_7$F$_{15}$, —Si(Me)$_2$CH$_2$CH$_2$C$_8$F$_{17}$, —Si(Me) (CH$_2$CH$_2$C$_5$F$_{11}$)$_2$, —Si(Me)(CH$_2$CH$_2$C$_6$F$_{13}$)$_2$, etc. Additional "non-incremental" tags can be generated without changing the numbers of fluorines on the tag by changing the size or nature of the "spacer" functionality (in this example, "CH$_2$CH$_2$") or grafting organic groups onto the tag to modify its behavior relative to an ungrafted tag.

In several embodiments of the invention, the following steps are carried out: compound tagging, mixing of the tagged compounds, conducting one or more chemical reactions on the compound mixture to make a new product mixture, separating the mixture by a method that complements the tags, and removing the tags. Two embodiments of the invention are shown schematically in FIGS. 1a and 1b. FIG. 1a shows the synthesis of a mixture library where all the members are reacted identically; in other words n starting materials give n products. Starting materials S$^1$–S$^n$ are attached to a sequence of "tags" T$^1$–T$^n$. In FIG. 1a, the tags are fluorous tags that are represented as F$^1$–F$^n$. The tagged substrates are then mixed and taken through a step or sequence of steps to provide the mixture of tagged products F$^1$P$^1$–F$^n$P$^n$. This mixture is then separated by a separation technique complementary to the tag (for example, fluorous reverse phase chromatography). Finally, the tagged products are preferably individually cleaved (or detagged) to give the target products. The method is designed to separate the products based on the tag placed on the initial substrate. For example, certain organic reactions are well known to produce mixtures of stereoisomers and/or regioisomers or even non-isomeric products. Even though separations of these products may sometimes occur, the invention is designed primarily to separate the product(s) derived from one substrate bearing one tag from the product(s) derived from different substrates bearing different tags.

In a variant of the above embodiment, a mixture of substrates is tagged with the same tag and then mixed with other different substrates or mixtures of different substrates tagged with different tags. The separation of the tagged products then provides mixtures of product compounds bearing the same initial tag.

In FIG. 1b, tagged substrates are reacted in at least one of the following steps with a mixture of reactants (as opposed to a single reactant). If there are n substrates and o reactants and all reactions succeed, then n·o products result. Separation by the method complementary to the tag will then provide groups of products rather than individual pure products. Each group of products has the same fluorous tag. In some cases, the members of these groups of products may actually be separated from each other during the tagged-based separation, or they could be separated by traditional means after detagging. For some applications, final separation to pure components is not desirable, and the method is instead used to divide a library into known sub-libraries based on the original tag. Such ordered sub-libraries are useful in various methods of deconvolution.

The steps of tagging, mixing and reacting can be conducted in various orders or even combined. For example, in the embodiment in FIG. 1c, a single substrate can be reacted with a mixture of tagged reagents added either together or individually to give a mixture of tagged products. Subsequent separation of the mixture based on the tag (possibly after additional reactions) separates or sorts the products by tag. Detagging then gives the final products.

In a preferred embodiment of this invention, the tags are fluorinated groups (for example, F$^1$–F$^n$ in FIGS. 1a–1c) and the separation method is fluorous reverse phase chromatography. Fluorous reverse phase chromatography separates primarily by fluorine content, so tags $F^1$–$F^n$ vary by the number of fluorines.

In many embodiments of the present invention, tagging also aids in the separation of the tagged products from any excess reagents, reactants, catalysts, or their by-products because all of those components are untagged.

In one embodiment, the tags are charged groups such as ammonium salts, carboxylates, phosphates, etc. that differ in the total number of charges in each tag and the complementary separation method is electrophoresis or a related technique. When the molecules are generally similar in size, electrophoresis and related techniques generally separate by the total charge of a molecule, so members of the family of tags contain increasing numbers of positive or negative charges. After generating a mixture of tagged products, the mixture is separated with the tagged products being separated in order of charge. In a preferred embodiment of this aspect of the invention, the charged functional groups are masked with protecting groups during the tagging and/or reaction states. The protecting groups are preferably removed prior to the separation stage to reveal the charged groups on the tags. Charged groups are undesirable in many common types of organic reactions.

Protecting groups are commonly used in chemical synthesis schemes to mask (protect) reactive functionalities so that reactions can be selectivity carried out at other sites. Examples of common protecting groups include benzyl, acyl, trialkylsilyl and carbamate, among many others. See, for example, Greene, T. W., and Wuts, P. G. M., *Protective Groups in Organic Synthesis,* 3rd ed.; Wiley-Interscience: New York, (1999).

In another embodiment, the tags are oligomers, polymers, or dendrimers, and the complementary separation method is size exclusion chromatography. Size exclusion chromatography separates by molecular size, so members of the family of tags in this embodiment are increasingly larger. It is preferable in this embodiment that the tags be much larger that the initial substrate to be tagged, so that the tag and not the substrate dominates the difference in size between the family of tagged products.

In another embodiment, the tags are non-polar organic groups such as linear hydrocarbons, and the complementary separation method is standard or, preferably, reverse phase chromatography. Reverse phase chromatography separates primary by polarity, so a family of tags should be increasingly more (or less) polar. It is preferable in this method that the product component of the tagged products be generally similar in polarity, so that the tag and not the tagged component dominates the chromatographic separation. Or in the case in which the polarity of the products is known or can be estimated in advance, the less polar products are preferably attached to the less polar tags and vise-versa. In this way, the tagged-base separation is enhanced.

The tags of the present invention can, for example, be attached to the substrates through any kind of standard covalent bond. The tags themselves and the method of tagging are preferably chosen so that both the tags and the bond(s) attaching the tags to the substrates are stable to the conditions used in any subsequent reaction(s). In one embodiment, the tags play a dual role as protecting groups and serve both during the reaction sequence to protect a labile, sensitive, or problematic group and after the reaction to control the separation. In another embodiment, the tags serve as "traceless units". Traceless units are groups that can generally be replaced leaving no functional group trace of the attachment. During the detagging reactions, the tags can be cleaved by standard reactions, including reactions that further functionalize or diversify the products.

In addition to being attached directly to the substrate, the tags can also be attached through the intermediacy of a linker. Linkers are bifunctional (or polyfunctional) molecules that are used to bridge the tag and the substrate. They can be attached first to the tag and then to the substrate or first to the substrate and then to the tag. Linkers are commonly used, for example, in solid phase synthesis. The use of linkers in the attachment of fluorous groups or moieties to organic compounds is described in U.S. Pat. Nos. 5,859,247 and 5,777,121

The molecular weights of the compounds/substrates prior to attachment to the tags in the present invention are preferably less than about 1,000, more preferably less that about 750, and even more preferably less than 600. The molecular weights of the products after detachment of the tags are preferably less than about 2,000, more preferably less than about 1,500, and even more preferably less than 1,000.

A number of the features of the present invention are illustrated by the synthesis and separation of the three mixture libraries shown in FIG. 2. These examples, wherein a mixture of three substrates was reacted with four reactants, clearly subsume applications in which the mixture is reacted with only one of the four reagents. Three libraries of 12 compounds were made, as illustrated in FIG. 2. The reaction of the tagged substrates was the conjugate addition of aromatic thiols to unsaturated esters. The esters were chosen as the fluorous tagged components. All possible combinations of the three tags (x, y, z) with the three esters (1, 2, 3) were made to demonstrate that the separation was dictated primarily by the tag and not by the molecule that was tagged or the thiol.

An initial mixture library was made by tagging acids 1, 2, and 3 with tags x, y, and z, respectively. The tagged adducts 1x, 2y, and 3z were mixed and reacted with the four untagged thiols a-d resulting in a mixture of 12 adducts in 4 sets of three (with respect to the tag). To accomplish the separation by fluorous reverse phase chromatography, the mixture was then injected on a commercial Fluofix column and the HPLC trace was recorded with UV detection. The retention times of the products (as assigned by comparison to authentic, pure samples) are shown in FIG. 2 as library 1. FIG. 3 shows a raw HPLC trace of a similar library. The compounds elute in order of the fluorine content of the tag; a first group of peaks corresponds to all the products with the $C_6F_{13}$ tag (18–24 min); a second group of peaks corresponds to all the products with the $C_8F_{17}$ tag (29–33 min), and a third group of peaks corresponds to all the products with the $C_{10}F_{21}$ tag (34–35 min). Within these groups, the separation of peaks was surprisingly good. Indeed, as many as 11 of the 12 possible peaks were observed with only two compounds overlapping (see FIG. 3). The compounds eluted reliably in order based on the appended thiol: c before b before a before d. The t-butyl-bearing compounds d always eluted well after the other three, which were closely spaced. In a preparative separation, a reasonable fractionation into six samples was obtained in the following order: 1xa–c, 1d, 2ya–c, 2d, 3za–c, 3d. Thus, instead of obtaining three fractions of four compounds, three fractions of three compounds each and three fractions of one compound each were obtained. After detagging, the mixed fractions could be separated to give pure products.

To demonstrate that the primary separation is by the tag, two complementary sets of tagged precursors where the tags and the acid substrates were mixed and matched were prepared as follows: 1y/2z/3x and 1z/2x/3y. These sets were again reacted with the four thiols (libraries 2 and 3) with similar results to the first library. The primary separation was by the fluorous tag (all x before all y before all z) with a secondary separation by thiol. A close inspection of the data showed that there was an effect of the ester as well (comparison of samples across libraries is needed for this determination). These results show that compounds can be reliably tagged, mixed, reacted, and then separated in a fashion predetermined by the initial tag selection.

FIGS. 4 and 5 show an example of mixture synthesis of analogs of the natural product mappicine. This also illustrates the use of a "null tag" (a tag with no fluorines). The compound with the null tag emerges first in the final mixture separation, prior to all of the tagged compounds. The use of one or more null tags is advantageous because it allows more compounds to be separated than the number of tags. The synthesis is an improvement over a prior route to mappicine. Josien, H. and Curran, D. P., "Synthesis of (S)-mappicine and mappicine ketone via radical cascade reaction of isonitriles", Tetrahedron 53, 8881–8886 (1997). The preparations of the precursors shown in FIG. 4 are described in the Examples section and in FIG. 6.

The five precurscors 4a–e shown in FIG. 4 were each tagged with a different silyl group on the free alcohol. The null tag (octyldimethylsilyl) was attached to 4a, and fluorous tags of increasing fluorine content were tagged to 4b–e. The fluorous silyl bromides and triflate in FIG. 4 were prepared in situ by treatment of the corresponding silanes (RfCH$_2$CH$_2$(Me)$_2$SiH) with dibromine or with triflic acid. These preparations are described in the Examples section along with the preparation of the silanes.

Equimolar amounts of the five silyl ethers 5a–e were mixed, and reacted under standard conditions for the cascade radical annulation reaction of with a p-tolyl isonitrile (see FIG. 5). See, U.S. Pat. No. 5,859,247; U.S. Pat. No. 5,777,121; and Josien, H. and Curran, D. P., "Synthesis of (S)-mappicine and mappicine ketone via radical cascade reaction of isonitriles", Tetrahedron 53, 8881–8886 (1997). After completion of the reaction, the solvent was evaporated and the mappicine mixture was separated from the tin by-products by silica gel chromatography. The mappicine mixture was then separated by HPLC on a Fluofix column to give individual samples of 6a–e which eluted in order of the tag from the null tag up to the C$_{10}$F$_{21}$ tag. Elution times and yields are summarized in FIG. 5. Products 6a–e from the mixture experiment were identical to samples of these products prepared by conducting individual reactions of each precursor 5a–e with p-tolyl isonitrile. The final products 6a–e can be detagged under standard conditions for cleavage of silyl ethers to provide new analogs of the natural product mappicine.

EXAMPLE

Example 1

Synthesis of the Fluorous Silane Tags for FIG. 2

Example 1a

1-Bromo-4-(2-perfluorohexyl)ethylbenzene

To zinc powder (1.63 g, 25.0 mmol) under argon was added THF (4 ml) and 1,2-bromoethane (0.100 ml). The mixture was heated at reflux at 5 min and then cooled to room temperature. Chlorotrimethylsilane (0.100 ml) was added and the resulting mixture was stirred for 15 min at room temperature. A THF solution (20 ml) of 1-iodo-1H, 1H, 2H, 2H-perfluorooctane (10.0 g, 21.00 mmol) was added to the reaction mixture at 30° C. The reaction mixture was stirred for 15 h at room temperature. The mixture was added to a THF solution (20 ml) of tetrakis (triphenylphosphine)palladium (0.850 g, 0.735 mmol) and 1-bromo-4-iodobenzene (6.09 g, 21.5 mmol). The mixture was heated at 45° C. for 12 h, cooled, and partitioned between dichloromethane (20 ml) and FC-72 (40 ml). The organic layer was washed two times with FC-72 and evaporated. Purification of the residue by distillation under high vacuum (0.2 mmHg, 120° C.) afforded 5.06 g (48%) of desired product as colorless solid: mp 33–34° C.; IR (KBr) 2954, 1485, 1236, 1145, 1004, 974, 851, 697, 570, 535, and 507 cm$^{-1}$; $^1$H NMR (CDCl$_3$) δ7.46 (d, J=8.3 Hz, 2H), 7.11 (d, J=8.3 Hz, 2H), 2.90–2.85 (m, 2H), and 2.45–2.20 (m, 2H); $^{13}$C NMR (CDCl$_3$) δ138.15, 131.99, 130.15, 120.69, 120–110 (m), 32.83 (t), and 26.05; $^{19}$F NMR (CDCl$_3$, relative to CCl$_3$F) δ−79.61 (3F), −113.45 (2F), −120.73 (2F), −121.71 (2F), −122.34 (2F), and −124.99 (2F); Mass (EI) (rel intensity, %) m/z 505 (6), 504 (33), 503 (7), 502 (32, M$^+$), 423 (7), 172 (7), 171 (base peak), 170 (8), 169 (99), 153 (6), 133 (5), 109 (37), 104 (10), 103 (5), 90 (20), and 89 (7); HRMS Calcd for C$_{14}$H$_8$F$_{13}$Br: m/z 501.9602. Found: m/z 501.96134.

Example 1b

1-Bromo-4-(2-perfluorooctyl)ethylbenzene

The compound was prepared according to the procedure for the preparation of 1-bromo-4-(2-perfluorooctyl)ethylbenzene (example 1a). A THF solution (40 ml) of 1-iodo-1H, 1H, 2H, 2H-perfluorodecane (12.1 g, 21.00 mmol) was added to the suspension of zinc. After workup, removal of palladium residue from the crude product by column chromatography on silica gel with hexane/ethyl acetate=19/1 gave a mixture of product and 1-bromo-4-iodobenzene (6.75 g, product/starting compound=75/25, 46% yield). This mixture was used for the following transformation: Colorless solid; mp 45–48° C.; IR (KBr) 2998, 1723, 1370, 1224, 998, 804, 669, and 527 cm$^{-1}$; $^1$H NMR (CDCl$_3$) δ7.46 (d, J=8.3 Hz, 2H), 7.11 (d, J=8.3 Hz, 2H), 2.90–2.86 (m, 2H), and 2.45–2.18 (m, 2H); $^{13}$C NMR (CDCl$_3$) δ138.16, 132.00, 130.14, 120.70, 120.00–100.00 (m), 32.85 (t), and 26.06; $^{19}$F NMR (CDCl$_3$, relative to CCl$_3$F) δ−79.52 (3F), −113.39 (2F), −120.47 (2F), −120.69 (4F), −121.51 (2F), −122.25 (2F), and −124.89 (2F); Mass (EI) (rel intensity, %) m/z 606 (6), 602 (7, M$^+$), 523 (7), 172 (6), 171 (98), 170 (6), 169 (base peak), 153 (7), 133 (5), 109 (42), 104 (9) 91 (6), 90 (14), 89 (5), and 69 (6); HRMS Calcd for C$_{16}$H$_8$F$_{17}$Br: m/z 601.9538. Found: m/z 601.951328.

Example 1c

1-Bromo-4-(2-perfluorodecyl)ethylbenzene

This was prepared according to the procedure for the preparation of 1-bromo-4-(2-perfluorooctyl)ethylbenzene (example 1a). A THF solution (40 ml) of 1-iodo-1H, 1H, 2H, 2H-perfluorododecane (14.2 g, 21.00 mmol) was added to a suspension of zinc. After workup, removal of palladium residue from the crude product by column chromatography on silica gel with hexane/ethyl acetate=19/1 gave a mixture of product and 1-bromo-4-iodobenzene (8.09 g, product/starting compound=52/48, 40% yield). This mixture was used for the following transformation: Colorless solid; mp 64–69° C.; IR (KBr) 2951, 1489, 1347, 1204, 1145, 1073, 1018, 883, 808, 756, 650, 562, and 523 cm$^{-1}$; $^1$H NMR (CDCl$_3$) δ7.45 (d, J=8.4 Hz, 2H), 7.11 (d, J=8.4 Hz, 2H), 2.92–2.79 (m, 2H), and 2.45–2.26 (m, 2H); $^{13}$C NMR (CDCl$_3$) δ138.16, 132.00, 130.16, 120.69, 120.00–100.00 (m), 32.84 (t), and 26.05; $^{19}$F NMR (CDCl$_3$, relative to CCl$_3$F) δ–79.54 (3F), –113.41 (2F), –120.86 (10F), –121.52 (2F), –122.27 (2F), and –124.92 (2F); Mass (EI) (rel intensity, %) m/z 705 (15), 704 (83), 703 (20), 702 (91, M$^+$), 682 (8), 683 (10), 623 (13), 314 (26), 169 (43), 153 (17), 152 (base peak), 151 (29), 150 (13), 126 (13), 109 (14), 76 (7), and 75 (5); HRMS Calcd for C$_{18}$H$_8$F$_{21}$Br: m/z 701.9474. Found: m/z 701.9536.

Example 1d 4-(2-Perfluorohexyl)ethylbenzylalcohol

A 1.7M solution of n-butyllithium in hexane (1.17 ml, 1.99 mmol) was added dropwise to THF solution (2 ml) of 1-bromo-4-(2-perfluorohexyl)ethylbenzene (0.500 g, 1.99 mmol) at –40° C. under argon. The resulting mixture was stirred for 20 min at –40° C. N,N-Dimethylformamide (0.154 ml, 1.99 mmol) was added dropwise to the mixture. After 30 min, diluted hydrochloric acid was added, and the mixture was extracted with dichloromethane three times. The organic layer was dried with anhydrous sodium sulfate, and evaporated.

To the above residue was added ethanol (2 ml) and sodium borohydride (75.2 mg, 1.99 mmol). This mixture was stirred at 25° C. for 16 h. The mixture was diluted with hydrochloric acid, and then extracted with dichloromethane three times. The organic layer was dried over sodium sulfate and evaporated. Purification of the residue by column chromatography on silica gel with hexane/ethyl acetate=3/1 afforded 0.366 g (81%) of product: Colorless solid; mp 33–35° C.; IR (neat) 3889, 2954, 2871, 1367, 1318, 1235, 1140, 1083, 1101, 837, and 697 cm$^{-1}$; $^1$H NMR (CDCl$_3$) δ7.34 (d, J=8.0 Hz, 2H), 7.23 (d, J=8.0 Hz, 2H), 4.96 (s, 2H), 2.96–2.90 (m, 2H), 2.47–2.28 (m, 2H), and 1.80–1.50 (br, 1H); $^{13}$C NMR (CDCl$_3$) δ139.47, 138.71, 128.63, 127.62, 120.00–103.00 (m), 65.17, 33.07 (t), and 26.27; $^{19}$F NMR (CDCl$_3$, relative to CCl$_3$F) δ–79.54 (3F), –13.46 (2F), –120.73 (2F), –121.71 (2F), –122.34 (2F), and –124.97 (2F); Mass (EI) (rel intensity, %) m/z 454 (21, M$^+$), 121 (18), 109 (7), 106 (13), 107 (base peak), 105 (5), 93 (7), 91 (31), 79 (47), 78 (7), 77 (22), and 60 (5); HRMS Calcd for C$_{15}$H$_{11}$F$_{13}$O: m/z 454.0602. Found: m/z 454.0589.

Example 1e 4-(2-Perfluorooctyl)ethylbenzylalcohol

This was prepared according to the procedure for the preparation of 4-(2-perfluorohexyl)ethylbenzylalcohol (Example 1d). Use of 1.7 M of n-butyllithium in hexane (14.6 ml, 24.9 mmol), N,N-dimethylformamide (1.93 ml, 24.9 mmol), THF (16 ml), and sodium borohydride (0.941 g, 24.9 ml) for treatment of the mixture (5.00 g) of 1-bromo-4-(2-perfluorooctyl)ethylbenzene/1-bromo-4-iodobenzene= 75:25) afforded 2.70 g (68%) of product: Colorless solid; mp 68–69° C.; IR (KBr) 3394, 2996, 1612, 1343, 1152, 1081, 1006, 883, 646, and 554 cm$^{-1}$; $^1$H NMR (CDCl$_3$) δ7.36 (d, J=8.0 Hz, 2H), 7.23 (d, J=8.0 Hz, 2H), 4.96 (s, 2H), 2.96–2.90 (m, 2H), 2.47–2.28 (m, 2H), and 1.90–1.70 (br, 1H); $^{13}$C NMR (CDCl$_3$) δ139.47, 138.70, 128.63, 127.62, 120.00–103.00 (m), 65.16, 33.06 (t), and 26.25; $^{19}$F NMR (CDCl$_3$, relative to CCl$_3$F) δ–79.55 (3F), –113.39 (2F), –120.53 (2F), –121.71 (2F), –122.29 (2F), and –124.91 (2F); Mass (EI) (rel intensity, %) m/z 555 (24), 554 (base peak, M$^+$), 553 (23), 552 (15), 551 (30), 537 (10), 536 (8), 535 (27), 525 (5), 167 (5), 121 (16), 109 (10), 108 (8), 107 (94), 105 (8), 91 (29), 79 (18), and 77 (6); HRMS Calcd for C$_{17}$H$_{11}$F$_{17}$O: m/z 554.0538. Found: m/z 554.0527.

Example 1f 4-(2-Perfluorodecyl)ethylbenzylalcohol

This was prepared according to the procedure for the preparation of 4-(2-perfluorohexyl)ethylbenzylalcohol (Example 1d). Use of 1.7 M of n-butyllithium in hexane (15.1 ml, 25.6 mmol), N,N-dimethylformamide (1.98 ml, 25.6 mmol), THF (16 ml), and sodium borohydride (0.968 g, 25.6 ml) for treatment of the mixture (6.00 g) of 1-bromo-4-(2-perfluorodecyl)ethylbenzene/1-bromo-4-iodobenzene= 52:48) afforded 3.04 g (75%) of product: Colorless solid; mp 95–97° C.; IR (KBr) 3366, 2958, 1706, 1370, 1335, 1208, 1149, 1081, 1013, 828, 700, 653, and 558 cm$^{-1}$; $^1$H NMR (CDCl$_3$) δ7.35 (d, J=8.0 Hz, 2H), 7.23 (d, J=8.0 Hz, 2H), 4.70 (s, 2H), 3.00–2.90 (m, 2H), 2.47–2.19 (m, 2H), and 1.80–1.50 (br, 1H); $^{13}$C NMR (CDCl$_3$) δ139.47, 138.72, 128.63, 121.00–100.00 (m), 65.17, 33.06 (t), and 26.26; $^{19}$F NMR (CDCl$_3$, relative to CCl$_3$F) δ–79.51 (3F), –113.41 (2F), –120.54 (2F), –121.48 (10F), –122.25 (2F), and –124.91 (2F); Mass (EI) (rel intensity, %) m/z 655 (6), 654 (30, M$^+$), 653 (7), 652 (20), 635 (11), 121 (18), 109 (9), 108 (7), 107 (base peak), 105 (8), 91 (28) and 79 (18); HRMS Calcd for C$_{19}$H$_{11}$F$_{21}$O: m/z 654.0474. Found: m/z 654.0463.

Example 2

Synthesis of Unsaturated Esters

Example 2a 4-(2-Perfluorohexyl)ethylbenzyl crotonate (1x)

Sodium hydride (about 1 mg) and ethyl crotonate (27.4 μl, 1.10 mmol) were added to a benzene solution (2 ml) of 4-(2-perfluorohexyl)ethylbenzylalcohol (0.100 g, 0.220 mmol), and then the mixture was heated at reflux for 1 h. Benzene was distilled out at atmospheric pressure to give a residue. The residue was quenched with dilute hydrochloric acid, and this mixture was extracted with dichloromethane. The organic layer was dried over anhydrous sodium sulfate and evaporated. Purification of the residue by column chromatography on silica gel with hexane/ethyl acetate=19/1 afforded 84 mg (73%) of product: Colorless oil; IR (neat) 2953, 1724, 1654, 1448, 1320, 1243, 1177, 1142, 1022, 975, 847, 808, and 711 cm$^{-1}$; $^1$H NMR (CDCl$_3$) δ7.34 (d, J=8.0 Hz, 2H), 7.22 (d, J=8.0 Hz, 2H), 7.03 (dq, J=15.3 Hz and J=7.0 Hz, 1H), 5.90 (dq, J=15.3 Hz and J=1.6 Hz, 1H), 5.18 (s, 2H), 2.96–2.85 (m, 2H), 2.47–2.28 (m, 2H), and 1.89 (dd, J=7.0 Hz and J=1.6 Hz, 3H); $^{13}$C NMR (CDCl$_3$) δ166.43, 145.38, 139.24, 134.85, 128.60, 128.60, 122.54, 120.00–103.00 (m), 65.74, 33.02 (t), 26.28, and 18.10; 19F NMR (CDCl$_3$, relative to CCl$_3$F) δ–79.62 (3F), –113.51 (2F), –120.75 (2F), –121.73 (2F), –122.38 (2F), and –125.01 (2F); Mass (EI) (rel intensity, %) m/z 522 (13, M+), 477 (10), 439 (26), 117 (10), 104 (13), 91 (12), and 69 (base peak); HRMS Calcd for C$_{19}$H$_{15}$F$_{13}$O$_2$: m/z 522.0864. Found: m/z 522.0873.

Example 2b 4-(2-Perfluorohexyl)ethylbenzyl 2-hexenoate (2x)

This was prepared according to the procedure for the preparation of 4-(2-perfluorohexyl)ethylbenzyl crotonate (1x): Colorless oil; IR (neat) 2960, 1724, 1654, 1464, 1375, 1239, 1173, 1014, 975, 812, 707, and 653 cm$^{-1}$; $^1$H NMR (CDCl$_3$) δ7.35 (d, J=8.0 Hz, 2H), 7.22 (d, J=8.0 Hz, 2H), 7.02 (dt, J=15.5 Hz and J=7.0 Hz, 1H), 5.87 (d, J=15.5 Hz, 1H), 5.16 (s, 2H), 2.96–2.86 (m, 2H) 2.50–2.30 (m, 2H), 2.29–2.05 (m, 2H), 1.65–1.44 (m, 2H), and 0.94 (t, J=7.4 Hz, 3H); $^{13}$C NMR (CDCl$_3$) δ166.66, 150.20, 139.25, 134.84, 128.88, 128.62, 121.10, 120.00–105.00 (m), 65.79, 34.38, 33.01 (t), 26.27, 21.33, and 13.78; $^{19}$F NMR (CDCl$_3$, relative to CCl$_3$F) δ–79.60 (3F), –113.48 (2F), –120.72 (2F), –121.70 (2F), –122.35 (2F), and –124.97 (2F); Mass (EI) (rel intensity, %) m/z 550 (28, M+), 494 (10), 438 (19), 437 (base peak), 117(25), 104 (29), 97 (99), 91 (32), 77 (10), and 56 (11); HRMS Calcd for C$_{21}$H$_{19}$F$_{13}$O$_2$: m/z 550.1177. Found: m/z 550.1202.

Example 2c 4-(2-Perfluorohexyl)ethylbenzyl methacrylate (3x)

This was prepared according to the procedure for the preparation of 4-(2-perfluorohexyl)ethylbenzyl crotonate (1x): Colorless oil; IR (KBr) 2959, 1720, 1634, 1456, 1320, 1243, 1014, 940, 816, 704, and 650 cm$^{-1}$; $^1$H NMR (CDCl$_3$) δ7.36 (d, J=8.0 Hz, 2H), 7.25 (d, J=8.0 Hz, 2H), 6.17 (s, 1H), 5.60 (s 1H), 5.19 (s, 2H), 2.97–2.64 (m, 2H), 2.47–2.29 (m, 2H), and 1.98 (s, 3H); $^{13}$C NMR (CDCl$_3$) δ167.44, 139.34, 136.44, 134.90, 128.79, 128.70, 126.03, 120.00–105.00 (m), 66.28, 33.10 (t), 26.37, and 18.52; $^{19}$F NMR (CDCl$_3$, relative to CCl$_3$F) δ–79.73 (3F), –113.55 (2F), –120.78 (2F), –121.77 (2F), –122.41 (2F), and –125.06 (2F); Mass (EI) (rel intensity, %) m/z 523 (15), 522 (73, M+), 504 (10), 478 (13), 477 (61), 453 (18), 451 (13), 438 (21), 437 (base peak), 118 (16), 104 (18), 91 (29), and 69 (80); HRMS Calcd for C$_{19}$H$_{15}$F$_{13}$O$_2$: m/z 522.0864. Found: m/z 522.0852.

Example 2d 4-(2-Perfluorooctyl)ethylbenzyl crotonate (1y)

This was prepared according to the procedure for the preparation of 4-(2-perfluorohexyl)ethylbenzyl crotonate (1x): Colorless solid; mp 33–34° C.; IR (KBr) 2934, 1710, 1651, 1450, 1378, 1200, 1145, 1105, 1022, 986, 804, 741, 665, and 554 cm$^{-1}$; $^1$H NMR (CDCl$_3$) δ7.34 (d, J=8.0 Hz, 2H), 7.22 (d, J=8.0 Hz, 2H), 7.03 (dq, J=15.5 Hz and J=6.9 Hz, 1H), 5.90 (dq, J=15.5 Hz and J=1.4 Hz, 1H), 5.14 (s, 2H), 2.96–2.89 (m, 2H), 2.46–2.28 (m, 2H), and 1.89 (dd, J=6.9 Hz and J=1.4 Hz, 3H); $^{13}$C NMR (CDCl$_3$) δ166.45, 145.42, 139.24, 134.83, 128.84, 128.61, 122.53, 120.00–105.00 (m), 65.76, 33.03 (t), 26.47, and 18.13; $^{19}$F NMR (CDCl$_3$, relative to CCl$_3$F) δ–79.55 (3F), –13.46 (2F), –120.52 (2F), –120.73 (4F), –121.54 (2F), –122.30 (2F), and –124.94 (2F); Mass (EI) (rel intensity, %) m/z 627 (14), 622 (27, M+), 604 (13), 577 (23), 553 (13), 551 (11), 538 (16), 537 (72), 309 (20), 308 (75), 265 (43), 223 (44), 180 (28), 1.79 (21), 178 (34), 165 (19), 117 (14), 104 (12), 91 (16), 69 (base peak), and 57 (12); HRMS Calcd for C$_{21}$H$_{15}$F$_{17}$O$_2$: m/z 622.0800. Found: m/z 622.0808.

Example 2e 4-(2-Perfluorooctyl)ethylbenzyl 2-hexenoate (2y)

This was prepared according to the procedure for the preparation of 4-(2-perfluorohexyl)ethylbenzyl crotonate (1x): Colorless solid; mp 33–34° C.; IR (neat) 2950, 2712, 1653, 1460, 1373, 1330, 1217, 1145, 978, 704, 656 and 561 cm$^{-1}$; $^1$H NMR (CDCl$_3$) δ7.36 (d, J=8.0 Hz, 2H), 7.23 (d, J=8.0 Hz, 2H), 7.03 (dt, J=15.6 Hz and J=7.0 Hz, 1H), 5.97 (d, J=15.6 Hz, 1H), 5.17 (s, 2H), 2.96–2.90 (m, 2H), 2.47–2.28 (m, 2H), 2.23–2.09 (m, 2H), 1.57–1.44 (m, 2H), and 0.95 (t, J=7.4 Hz, 3H); $^{13}$C NMR (CDCl$_3$) δ166.64, 150.16, 139.25, 134.85, 128.86, 128.59, 121.10, 120.00–103.00 (m), 65.77, 34.36, 33.01 (t), 26.26, 21.32, and 13.72; $^{19}$F NMR (CDCl$_3$, relative to CCl$_3$F) δ–79.80 (3F), –113.60 (2F), –120.64 (2F), –120.87 (4H), –121.68 (2F), –122.41 (2F), and –125.10 (2F); Mass (EI) (rel intensity, %) m/z 650 (3, M+), 594 (5), 590 (5), 551 (9), 538 (17), 537 (base peak), 178 (15), 177 (10), 176 (13), 115 (7), 102 (5), and 98 (5); HRMS Calcd for C$_{23}$H$_{19}$F$_{17}$O$_2$: m/z 650.1113. Found: m/z 650.1125.

Example 2f 4-(2-Perfluorooctyl)ethylbenzyl methacrylate (3y)

This was prepared according to the procedure for the preparation of 4-(2-perfluorohexyl)ethylbenzyl crotonate (1x): Colorless oil: IR (neat) 2953, 1724, 1638, 1456, 1371, 1200, 1154, 944, 812, and 657 cm$^{-1}$; $^1$H NMR (CDCl$_3$) δ7.36 (d, J=8.0 Hz, 2H), 7.23 (d, J=8.0 Hz, 2H), 6.17 (s, 1H), 5.60 (s 1H), 5.19 (s, 2H), 2.96–2.80 (m, 2H), 2.48–2.28 (m, 2H), and 1.99 (s, 3H); $^{13}$C NMR (CDCl$_3$) δ167.44, 139.34, 136.44, 134.90, 128.79, 128.69, 126.02, 124.00–106.00 (m), 66.28, 33.11 (t), 26.38, and 18.51; $^{19}$F NMR (CDCl$_3$, relative to CCl$_3$F) δ–79.74 (3F), –113.56 (2F), –120.60 (2F), –120.83 (4H), –121.64 (2F), –122.38 (2F), and –125.06 (2F); Mass (EI) (rel intensity, %) m/z 622 (8, M+), 577 (33), 551 (23), 538 (20), 537 (base peak), 165 (13), 129 (17), 128 (23), 116 (12), 115 (26), 103 (34), 89 (23), 84 (12), and 83 (17); HRMS Calcd for C$_{21}$H$_{15}$F$_{17}$O$_2$: m/z 622.0800. Found: m/z 622.0804.

Example 2g 4-(2-Perfluorodecyl) ethylbenzyl crotonate (1z)

This was prepared according to the procedure for the preparation of 4-(2-perfluorohexyl)ethylbenzyl crotonate (1x): Colorless solid; mp 46–48° C.; IR (KBr) 2939, 1715, 1655, 1450, 1196, 1149, 986, 887, 646, 558, and 531 cm$^{-1}$; $^1$H NMR (CDCl$_3$) δ7.35 (d, J=8.0 Hz, 2H), 7.22 (d, J =8.0 Hz, 2H), 6.98 (dq, J=15.7 Hz and J=7.0 Hz, 1H), 5.90 (dq, J=15.7 Hz and J=1.5 Hz, 1H), 5.15 (s, 2H), 2.96–2.90 (m, 2H), 2.60–2.44 (m, 2H), and 1.88 (dd, J=7.0 Hz and J=1.5 Hz, 3H); $^{13}$C NMR (CDCl$_3$) δ166.45, 145.41, 139.25, 134.84, 128.84, 128.60, 122.53, 120.00–105.00 (m), 65.75, 33.01 (t), 26.25, and 18.11; $^{19}$F NMR (CDCl$_3$, relative to CCl$_3$F) δ–79.67 (3F), –113.52 (2F), –120.65 (10F), –121.59 (2F), –122.35 (2F), and –125.02 (2F); Mass (EI) (rel intensity, %) m/z 722 (11, M+), 704 (14), 678 (13), 677 (53), 676 (14), 654 (23), 651 (25), 638 (22), 637 (base peak), 171 (14), 167 (18), 166 (11), 165 (28), 163 (10), 154 (10), 148 (14), 147 (15), 144 (15), 133 (17), 130 (14), 129 (11), 128 (26), 127 (12), 126 (16), 125 (12), 105 (11), 104 (43), 103 (19), 102 (13), and 89 (22); HRMS Calcd for C$_{23}$H$_{15}$F$_{21}$O$_2$: m/z 722.0736. Found: m/z 722.0729.

Example 2h 4-(2-Perfluorodecyl)ethylbenzyl 2-hexenoate (2 z)

This was prepared according to the procedure for the preparation of 4-(2-perfluorohexyl)ethylbenzyl crotonate (1x): Colorless solid; mp 36–38° C.; IR (neat) 2958, 1719, 1655, 1465, 1382, 1223, 1150, 978, 879, 645, and 554 cm$^{-1}$; $^1$H NMR (CDCl$_3$) δ7.35 (d, J=8.0 Hz, 2H), 7.23 (d, J=8.0

Hz, 2H), 7.03 (dt, J=15.5 Hz and J=7.0 Hz, 1H), 5.88 (dd, J=15.6 Hz and J=1.5 Hz, 1H), 5.16 (s, 2H), 2.96–2.85 (m, 2H), 2.50–2.33 (m, 2H), 2.23–2.13 (m, 2H), 1.56 –1.40 (m, 2H), and 0.95 (t, J=7.4 Hz, 3H); $^{13}$C NMR (CDCl$_3$) δ166.58, 150.10, 139.19, 134.76, 128.80, 128.52, 121.02, 120.00–105.00 (m), 65.71, 34.30, 32.94 (t), 26.20, 21.25, and 13.66; $^{19}$F NMR (CDCl$_3$, relative to CCl$_3$F) δ–79.58 (3F), –113.46 (2F), –120.58 (10F), –121.53 (2F), –122.30 (2F), and –124.95 (2F); Mass (EI) (rel intensity, %) m/z 750 (5, M$^+$), 725 (6), 653 (10), 638 (18), 637 (91), 537 (9), 223 (6), 179 (28), 178 (base peak), 164 (43), 121 (23), 117 (18), 115 (12), 104 (14), 97 (59), 91 (32), 68 (15), and 56 (14); HRMS Calcd for C$_{25}$H$_{19}$F$_{21}$O$_2$: m/z 750.1049. Found: m/z 750.1054.

Example 2i 4-(2-Perfluorodecyl)ethylbenzyl methacrylate (3z)

This was prepared according to the procedure of the preparation of 4-(2-perfluorohexyl)ethylbenzyl crotonate (1x): Colorless solid; mp 55–56° C.; IR (KBr) 2950, 1897, 1723, 1652, 1450, 1374, 1212, 1149, 1081, 880, 642, and 558 cm$^{-1}$; $^1$H NMR (CDCl$_3$) δ7.35 (d, J=8.0 Hz, 2H), 7.23 (d, J =8.0 Hz, 2H), 6.17 (s, 1H), 5.60 (s, 1H), 5.19 (s, 2H), 2.97–2.90 (m, 2H), 2.45–2.28 (m, 2H), and 1.98 (s, 3H); $^{13}$C NMR (CDCl$_3$) δ167.37, 139.24, 136.31, 134.77, 128.70, 128.61, 125.99, 122.00–100.00 (m), 66.19, 33.01 (t), 26.27, and 18.45; $^{19}$F NMR (CDCl$_3$, relative to CCl$_3$F) δ–79.59 (3F), –113.50 (2F), –120.59 (10F), –121.56 (2F), –122.31 (2F), and –124.96 (2F); Mass (EI) (rel intensity, %) m/z 722 (19, M$^+$), 677 (15), 637 (27), 537 (10), 177 (19), 178 (68), 169 (17), 167 (16), 166 (10), 165 (44), 121 (18), 199 (13), 117 (31), 104 (31), and 69 (base peak); HRMS Calcd for C$_{23}$H$_{15}$F$_{21}$O$_2$: m/z 722.0736. Found: m/z 722.0719.

Example 3

General Procedure for the Synthesis of Individual Michael Adducts

Twelve separate acceptor solutions (4 each of 1x, 2y, and 3z) were prepared by diluting an acceptor (0.05 mmol) with THF (50 ul). One of the four thiols (0.25 mmol, benzenethiol, 2-naphthalenethiol, 4-methoxybenzenethiol, and 4-tert-butylbenzenethiol) was added to each of the twelve acceptor solutions such that all possible combinations of three acceptors and four thiols were generated. Triethylamine (6.1 μl, 0.05 mol) was added to each mixture. The mixtures were stirred for 15 h at room temperature. The reaction mixtures were charged on to 3.00 g of fluorous reverse phase silica gel in twelve short columns with methanol/water=4/1. The columns were eluted with methanol/water=4/1 (12 ml), and then they were eluted with ethyl acetate (12 ml). Removal of solvent of the ethyl acetate fractions gave the twelve individual Michael adducts. These were used as standards to characterize the mixture library. The characterization data of 4-(2-perfluorodecyl) ethylbenzyl 2-methyl-3-phenylthiopropanate (3az) are representative: 4-(2-perfluorodecyl)ethylbenzyl 2-methyl-3-phenylthiopropanate (3az): Colorless solid; mp 51–52° C.; IR (KBr) 2954, 1731, 1592, 1236, 887, 816, 737, 650, and 554 cm$^{-1}$; $^1$H NMR (CDCl$_3$) δ7.39–7.17 (m, 9H), 5.10 (s, 2H), 3.29 (dd, J=13.2 Hz and J=7.3 Hz, 1H), 2.96 (dd, J=13.2 Hz and J=7.0 Hz, 1H), 2.95–2.85 (m, 2H), 2.80–2.70 (s, 1H), 2.50–2.25 (m, 2H), and 1.30 (d, J=7.1 Hz, 3H); $^{13}$C NMR (CDCl$_3$) δ174.86, 139.33, 135.76, 134.52, 130.19, 129.10, 128.76, 128.62, 126.61, 120.00–105.00 (m), 66.25, 39.92, 37.47, 32.98 (t), 26.28, and 16.88; $^{19}$F NMR (CDCl$_3$, relative to CCl$_3$F) δ–79.60 (3F), –113.46 (2F), –120.59 (10H), –121.55 (2F), –122.31 (2F), and –124.96 (2F); Mass (EI) (rel intensity, %) m/z 833 (10), 832 (30, M$^+$), 638 (16), 637 (93) 205 (14) 196 (13), 195 (base peak), 177 (12), 152 (31), 149 (37), 139 (16), 137 (19) 131 (21), 124 (46), 120 (12), 118 (40) 110 (16), 109 (49) 107 (12), 105 (21), and 104 (35); HRMS Calcd for C$_{29}$H$_{21}$F$_{21}$O$_2$S: m/z 832.0944. Found: m/z 832.0947.

Example 4

Representative Procedure for Michael Addition of 4 Thiols with 3 Acceptors (LC-Mass analysis)

Benzenethiol (20.6 μl, 0.200 mmol), naphthalenethiol (32.1 mg, 0.200 mmol), 4-methoxybenzenethiol (24.6 μl, 0.200 mmol), 4-tert-butylbenzenethiol (33.6 μl, 0.200 mmol), and triethylamine (18.3 μl, 0.15 mmol) were added to a THF solution (150.0 μl) of the three acceptors (1x, 2y, 3z, 0.05 mmol each). The mixture was stirred for 15 h at room temperature. The reaction mixture was then charged on to 5.00 g of fluorous reverse phase silica gel in short column wetted with methanol/water=4/1. The column was eluted first with 20 ml of methanol/water=4/1, and then with 20 ml of ethyl acetate. Evaporation of the ethyl acetate fraction gave the mixture of Michael adducts. The mixture was analyzed by LC-MS (APCI, positive mode) with a Fluofix 120E (1E415, 150×4.6 mm) column (MeOH/H$_2$O= 4/1 gradient to MeOH only for 40 min, flow rate 1.0 ml/min). All twelve adducts were present as evidenced by the presence of the molecular ions in the MS. Retention times for the peaks are shown in FIG. 2 as entry 1.

Example 5

General Procedure for Michael Addition of 3 Thiols with 3 Acceptors to Form a Mixture Library (Separation by HPLC)

Naphthalenethiol (8.0 mg, 0.050 mmol), 4-methoxybenzenethiol (6.2 μl, 0.0500 mmol), 4-tert-butylbenzenethiol (8.4 μl, 0.050 mmol), and DBU (7.5 μl, 0.050 mmol) were added to a THF solution (150.0 μl) of 3 acceptors (0.05 mmol of 1y, 2z, 3x). The mixture was stirred for 5 h at room temperature. The reaction mixture was then charged onto 5.00 g of fluorous reverse phase silica gel in short column wetted with methanol/water=4/1. The column was eluted with 20 ml of methanol/water=4/1, and then with 20 ml of ethyl acetate. Evaporation of the ethyl acetate, fraction gave the mixture of Michael adducts.

This mixture was separated into 6 fractions: 1) a mixture of 3xb, and 3xc, 2) 3xd, 3) a mixture of 1 yb, and 1yc, 4) a mixture of 1 yd, 5) a mixture of 2 zb, and 2 zc, 6) 2 zd] by HPLC (Fluofix 120E, 1EW125, 250×10.0 mm, NEOS Co. Ltd.) (MeOH/H$_2$O=4/1 gradient to MeOH only for 60 min, flow rate 3.0 ml/min). The mixtures 1), 3), and 5) were further separated by HPLC (Nova-pack 250×100 mm, Waters Corp.) (MeOH/H$_2$O=19/1 to MeOH only for 30 min, flow rate 5.0 ml/min) into the individual components.

Two other libraries were prepared similarly using different combinations of tags and esters, as shown in FIG. 2. Data for the products follow:

1xa: $^1$H NMR (CDCl$_3$) δ7.46–7.20 (m, 9H), 5.10 (s, 2H), 3.66–3.60 (m, 1H), 2.96–2.90 (m, 2H), 2.69 (dd, J=15.7 Hz and J=6.1 Hz, 1H), 2.49 (dd, J=15.7 Hz and J=8.5 Hz, 1H), 2.45–2.30 (m, 2H), and 1.33 (d, J=6.9 Hz, 3H).

1xb: $^1$H NMR (CDCl$_3$) δ8.00–7.19 (m, 11H), 5.09 (s, 2H), 3.80–3.74 (m, 1H), 2.95–2.89 (m, 2H), 2.74 (dd, J=15.6

Hz and J=6.2 Hz, 1H), 2.54 (dd, J=15.6 Hz and J=8.3 Hz, 1H), 2.49–2.30 (m, 2H) and 1.38 (d, J=6.8 Hz, 3H)

1xc: $^1$H NMR (CDCl$_3$) δ7.43–7.21 (m, 6H), 6.87–6.79 (m, 2H), 5.06 (s, 2H), 3.81 (s, 3H), 3.49–3.42 (m, 1H), 2.96–2.88 (m, 2H), 2.64 (dd, J=15.5 Hz and J=6.3 Hz, 1H), 2.44 (dd, J=15.5 Hz and J=8.2 Hz, 1H), 2.48–2.28 (m, 2H), and 1.21 (d, J=6.9 Hz, 3H)

1xd: $^1$H NMR (CDCl$_3$) δ7.47–7.17 (m, 8H), 5.10 (s, 2H), 3.63–3.58 (m, 1H), 2.96–2.90 (m, 2H), 2.70 (dd, J=15.6 Hz and J=6.1 Hz, 1H), 2.47 (dd, J=15.6 Hz and J=8.4 Hz, 1H), 2.52–2.34 (m, 2H), 1.32 (d, J=6.8 Hz, 3H), and 1.31 (s, 9H).

2ya: $^1$H NMR (CDCl$_3$) δ7.52–7.10 (m, 9H), 5.09 (s, 2H), 3.53–3.48 (m, 1H) 2. 95–2.89 (m, 2H), 2.70–2.55 (m, 2H), 2.45–2.30 (m, 2H), 1.70–1.40 (m, 4H), and 0.90 (t, J=6.9 Hz, 3H)

2yb: $^1$H NMR (CDCl$_3$) δ7.90–7.17 (m, 11H) 5.07 (s, 2H) 3.70–3.61 (m, 1H), 2.95–2.88 (m, 2H), 2.69–2.60 (m, 2H), 2.49–2.30 (m, 2H), 1.70–1.27 (m, 4H), and 0.92 (t, J=7.0 Hz, 3H).

2yc: 1H NMR (CDCl$_3$) δ7.42–7.20 (m, 6H), 6.85–6.78 (m, 2H), 5.10 (s, 2H), 3.80 (s, 3H), 3.33–3.29 (m, 1H), 2.96–2.89 (m, 2H), 2.60–2.49 (m, 2H), 2.48–2.30 (m, 2H), 1.70–1.40 (m, 4H), and 0 89 (t, J=6.8 Hz, 3H).

2yd: $^1$H NMR (CDCl$_3$) δ7.47–7.20 (m, 8H), 5.09 (s, 2H) 3.50–3.43 (m, 1H), 2.96–2.90 (m, 2H), 2.70–2.55 (m, 2H), 2.50–2.30 (m, 2H), 1.70–1.40 (m, 4H), 1.31 (s, 9H), and 0.90 (t, J=6.6 Hz, 3H).

3za: Colorless solid; mp 51–52° C.; IR (KBr) 2954, 1731, 1592, 1236, 887, 816, 737, 650, and 554 cm$^{-1}$; $^1$H NMR (CDCl$_3$) δ7.39–7.17 (m, 9H), 5.10 (s, 2H), 3.29 (dd, J=13.2 Hz and J=7.3 Hz, 1H), 2.96 (dd, J=13.2 Hz and J=7.0 Hz, 1H), 2.95–2.85 (m, 2H), 2.80–2.70 (s, 1H), 2.50–2.25 (m, 2H), and 1.30 (d, J=7.1 Hz, 3H); $^{13}$C NMR (CDCl$_3$) δ174.86, 139.33, 135.76, 134.52, 130.19, 129.10, 128.76, 128.62, 126.61, 120.00–105.00 (m), 66.25, 39.92, 37.47, 32.98 (t), 26.28, and 16.88; $^{19}$F NMR (CDCl$_3$, relative to CCl$_3$F) δ–79.60 (3F), –113.46 (2F), –120.59 (10H), –121.55 (2F), –122.31 (2F), and –124.96 (2F); Mass (EI) (rel intensity, %) m/z 833 (10), 832 (30, M$^+$), 638 (16), 637 (93), 205 (14), 196 (13), 195 (base peak), 177 (12), 152 (31), 149 (37), 139 (16), 137 (19), 131 (21), 124 (46), 120 (12), 118 (40), 110 (16), 109 (49), 107 (12), 105 (21), and 104 (35). HRMS Calcd for C$_{29}$H$_{21}$F$_{21}$O$_2$S: m/z 832.0944. Found: m/z 832.0947.

3zb: $^1$H NMR (CDCl$_3$) δ8.00–7.05 (m, 11H), 5.07 (s, 2H), 3.40 (dd, J=13.3 Hz and J=7.2 Hz, 1H), 3.07 (dd, J=13.3 Hz and J=6.8 Hz, 1H), 2.94–2.90 (m, 2H), 2.90–2.75 (m, 1H), 2.50–2.25 (m, 2H), and 1.33 (d, J=7.0 Hz, 3H).

3zc: $^1$H NMR (CDCl$_3$) δ7.39–7.20 (m, 6H), 6.86–6.79 (m, 2H), 5.08 (s, 2H), 3.80 (s, 3H), 3.16 (dd, J=13.3 Hz and J=7.5 Hz, 1H), 2.96–2.80 (m, 3H), 2.72–2.63 (m, 1H), 2.51–2.30 (m, 2H), and 1.26 (d, J=7.0 Hz, 3H).

3zd: $^1$H NMR (CDCl$_3$) δ7.51–7.19 (m, 8H), 5.09 (s, 2H) 3.26 (dd, J=13.3 Hz and J=7.3 Hz, 1H), 2.97–2.90 (m, 3H), 2.80–2.70 (m, 1H), 2.60–2.34 (m, 2H), 1.31 (s, 9H), and 1.27 (d, J=6.7 Hz, 3H).

3xb: $^1$H NMR (CDCl$_3$) δ7.82–7.15 (m, 11H), 5.09 (s, 2H), 3.38 (dd, J=13.3 Hz and J=7.2 Hz, 1H), 3.05 (dd, J=13.3 Hz and J=6.8 Hz, 1H), 2.95–2.90 (m, 2H), 2.90–2.75 (m, 1H), 2.50–2.30 (m, 2H), and 1.32 (d, J=7.0 Hz, 3H).

3xc: $^1$H NMR (CDCl$_3$) δ7.38–7.21 (m, 6H), 6.85–6.80 (m, 2H), 5.09 (s, 2H), 3.80 (s, 3H), 3.16 (dd, J=13.4 Hz and J=7.4 Hz, 1H), 2.96–2.90 (m, 2H), 2.84 (dd, J=13.4 Hz and J=6.7 Hz, 1H), 2.72–2.63 (m, 1H), 2.50–2.30 (m, 2H), and 1.20 (d, J=7.1 Hz, 3H).

3xd: $^1$H NMR (CDCl$_3$) δ7.38–7.20 (m, 8H), 5.08 (s, 2H), 3.25 (dd, J=13.3 Hz and J=7.2 Hz, 1H), 2.95–2.88 (m, 3H), 2.80–2.70 (m, 1H), 2.50–2.30 (m, 2H), 1.30 (s, 9H) and 1.27 (d, J=7.0 Hz, 3H).

1yb: $^1$H NMR (CDCl$_3$) δ7.90–7.00 (m, 11H), 5.08 (s, 2H), 3.80–3.72 (m, 1H), 2.95–2.88 (m, 2H), 2.73 (dd, J=15.6 Hz and J=6.1 Hz, 1H), 2.53 (dd, J=15.6 Hz and J=8.3 Hz, 1H), 2.39–2.20 (m, 2H), and 1.37 (d, J=6.9 Hz, 3H).

1yc: $^1$H NMR (CDCl$_3$) δ7.43–7.20 (m, 6H), 6.88–6.79 (m, 2H), 5.09 (s, 2H), 3.81 (s, 3H), 3.50–3.40 (m, 1H), 2.96–2.89 (m, 2H), 2.63 (dd, J=15.5 Hz and J=6.4 Hz, 1H), 2.44 (dd, J=15.5 Hz and J=8.0 Hz, 1H), 2.55–2.37 (m, 2H), and 1.27 (d, J=7.1 Hz, 3H). 1yd: $^1$H NMR (CDCl$_3$) δ7.39–7.20 (m, 8H), 5.09 (s, 2H), 3.62–3.53 (m, 1H), 2.96–2.89 (m, 2H), 2.47 (dd, J=15.6 Hz and J=8.1 Hz, 1H), 2.38 (dd, J=15.6 Hz and J=7.9 Hz, 1H), 2.37–2.20 (m, 2H), 1.31 (d, J=7.0 Hz, 3H), and 1.31 (s, 9H).

2zb: $^1$H NMR (CDCl$_3$) δ7.89–7.10 (m, 11H), 5.07 (s, 2H), 3.66–3.60 (m, 1H), 2.94–2.88 (m, 2H), 2.70–2.59 (m, 2H), 2.50–2.30 (m, 2H), 1.70–1.40 (m, 4H), and 0.90 (t, J=7.0 Hz, 3H).

2zc: $^1$H NMR (CDCl$_3$) δ7.41–7.10 (m, 6H), 6.85–6.80 (m, 2H), 5.09 (s, 2H), 3.80 (s, 3H), 3.33–3.28 (m, 1H), 2.96–2.89 (m, 2H), 2.57–2.50 (m, 2H), 2.50–2.20 (m, 2H), 1.70 –1.40 (m, 4H), and 0.89 (t, J=7.0 Hz, 3H).

2zd: $^1$H NMR (CDCl$_3$) δ7.38–7.20 (m, 8H), 5.09 (s, 2H), 3.50–3.40 (m, 1H), 2.96–2.89 (m, 2H), 2.70–2.50 (m, 2H), 2.50–2.30 (m, 2H), 1.70–1.40 (m, 4H), 1.31 (s, 9H), and 0.90 (t, J=6.8 Hz, 3H).

LC-Mass (M+1)
1xa=633; 1xb=683; 1xc=663; 1xd=689
2ya=761; 2yb=811; 2yc=791; 2yd=817
3za=833; 3zb=883; 3zc=863; 3zd=889
2xa=661; 2xb=711; 2xc=691; 2xd=717
3ya=733; 3yb=783; 3yc=763; 3yd=789
1za=833; 1zb=883; 1zc=863; 1zd=889
3xa=633; 3xb=683; 3xc=663; 3xd=689
1ya=733; 1yb=783; 1yc=763; 1yd=789
2za=861; 2zb=911; 2zc=891; 2zd=917

Example 6

General Procedure for the Deprotection of the Michael Adducts

Titanium tetraisopropoxide (12.5 mg, 0.0439 mmol) was added to a suspension of each Michael adduct (0.0240 mmol) in anhydrous 2-propanol (0.5 ml) under argon. The mixture was heated at reflux temperature for 6 h, cooled to room temperature, and was quenched with dilute hydrochloric acid. The resulting mixture was extracted with ethyl ether three times. The organic layer was dried over sodium sulfate and evaporated. The residue in a minimum amount of acetonitrile was charged on to 2.00 g of fluorous reverse phase silica gel in a short column wetted with methanol/water=4/1. The column was eluted with 8 ml of methanol/water=4/1 and then it was eluted with 8 ml of ethyl acetate to give fluorous tagged benzylalcohols. Removal of solvent from the first eluate and the second eluate afforded deprotected product and fluorous tagged benzylalcohol, respectively. 1-Methylethyl 2-methyl-3-phenylthiopropanate is a representative deprotected product.

1-Methylethyl 2-methyl-3-phenylthiopropanoate

Colorless oil; IR (KBr) 2979, 2929, 1728, 1585, 1458, 1315, 1211, 1170, 739, and 691 cm$^{-1}$; $^1$H NMR (CDCl$_3$) δ7.40–7.20 (m, 5H), 5.08–5.00 (m, 1H), 3.26 (dd, J=13.2 Hz and J=7.3 Hz, 1H), 2.92 (dd, J=13.2 Hz and J=6.9 Hz, 1H), 2.69–2.58 (m, 1H), and 1.27–1.22 (m, 6H); $^3$C NMR (CDCl$_3$) δ174.59, 136.02, 130.04, 129.07, 126.50, 68.11, 40.01, 37.46, 21.94, and 16.94; Mass (EI) (rel intensity, %) m/z 238 (7, M$^+$), 123 (8), 88 (14), 86 (71), and 84 (base peak); HRMS Calcd for C$_{13}$H$_{18}$O$_2$S: m/z 238.1044. Found: m/z 238.1016.

Example 7

Synthesis of the Iodopydridone Precursors for the Experiments in FIGS. 4 and 5 (See Flow Scheme Summary in FIG. 6)

Example 7a

4-Iodo-2-methoxy-3-methyl-6-trimethylsilylpyridine

To a solution of 4-iodo-2-methoxy-6-trimethylsilyl-3-pyridinecarboxaldehyde (1282 mg, 3.83 mmol) and Et$_3$SiH (1.6 mL, 6.13 mmol) cooled to 0° C. was added dropwise BF$_3$.OEt$_2$ (1.26 ml, 6.13 mmol). The mixture was stirred 2 h at 60° C. After cooling, brine was added, the aqueous layer was extracted with Et$_2$O and the organic layer was dried (MgSO$_4$) and evaporated. The residue was purified by flash chromatography (hexanes) to give the iodopyridine as a colorless oil (896 mg, 73%); $^1$H NMR (300 MHz, CDCl$_3$) δ7.47 (s, 1H), 3.96 (s, 3H), 2.33 (s, 3H), 0.29 (s, 9H) $^{13}$C NMR (75 MHz, CDCl$_3$) δ162.2, 160.9, 132.6, 124.3, 112.8, 53.7, 20.8, −1.9; HRMS (EI) m/z calcd for C$_{10}$H$_{16}$INOSi (M$^+$) 321.0034, found 321.0046; EIMS m/z 321 (M$^+$, 57), 306 (100).

Example 7b

General Procedure for Grignard Formation and Addition to Aldehydes

To a solution of the iodopyridine (3 mmol) in THF (10 mL) at −40° C. was added dropwise $^i$PrMgCl (1.3 equiv. 2.0 M in THF). The solution was stirred at that temperature for 30 min and then the appropriate aldehyde (1.6 equiv) was added neat and the reaction was stirred 1 h at −40° C. and 15 min at 23° C. It was diluted with Et$_2$O and washed with brine and extracted with Et$_2$O. The combined organic layers dried with Et$_2$O and evaporated and the residue was subjected to flash chromatography.

1-[2-Methoxy-3-methyl-6-(trimethylsilanyl)pyridin-4-yl]-propan-1-ol

Colorless oil (87%), flash chromatography (hexanes-EtOAc 20:1): $^1$H NMR (300 MHz, CDCl$_3$) δ7.22 (s, 1H), 4.88 (t, J=6.4 Hz, 1H), 3.98 (s, 3H), 2.13 (s, 3H), 1.92 (br s, 1H), 1.71 (quint, J=7.0 Hz, 2H), 0.99 (t, J=7.0 Hz, 3H), 0.29 (s, 9H); $^{13}$C NMR (75 MHz, CDCl$_3$) δ165.0, 164.5, 154.1, 122.3, 119.5, 74.9, 56.7, 34.1, 14.2, 13.7, 1.7; HRMS (EI) m/z calcd for C$_{13}$H$_{23}$NO$_2$Si (M$^+$) : 253.1499, found 253.1498; EIMS m/z 253 (M$^+$, 25), 238 (100).

1-[2-Methoxy-3-methyl-6-(trimethyl-silanyl)-pyridin-4-yl]-2,2-dimethyl-propan-1-ol Colorless oil (74%), flash chromatography (hexanes-EtOAc 15:1): $^1$H NMR (300 MHz, CDCl$_3$) δ7.21 (s, 1H), 4.75 (d, J=3.1 Hz, 1H), 3.96 (s, 3H), 2.13 (s, 3H), 1.87 (d, J=3.1 Hz, 1H), 0.90 (s, 9H), 0.28 (s, 9H); $^{13}$C NMR (75 MHz, CDCl$_3$) δ1.7, 159.6, 148.4, 121.5, 118.1, 76.3, 53.3, 36.9, 26.1, 12.4, −1.7; HRMS (EI) m/z calcd for C$_{15}$H$_{27}$NO$_2$Si (M$^+$): 281.1811, found: 281.1800; EIMS m/z 281 (M$^+$, 23), 266 (36), 225 (100).

1-[2-Methoxy-3-methyl-6-(trimethylsilanyl)pyridin-4-yl]-2-phenylethanol

Colorless oil (69%), flash chromatography (hexanes-EtOAc 15:1): $^1$H NMR (300 MHz, CDCl$_3$) δ7.38–7.23 (m, 6H), 5.10 (dd, J=8.6, 3.8 Hz, 1H), 4.01 (s, 3H), 3.00 (dd, J=13.9, 3.8 Hz, 1H), 2.85 (dd, J=13.8, 8.6, 1H), 2.13 (s, 3H), 2.09 (br s, 1H), 0.28 (s, 9H) $^{13}$C NMR (75 MHz, CDCl$_3$) δ161.7, 161.3, 149.9, 138.0, 129.6, 128.8, 126.9, 119.0, 116.0, 71.3, 53.4, 44.5, 10.9, −1.6; HRMS (EI) m/z calcd for C$_{18}$H$_{25}$NO$_2$Si (M$^+$): 315.1654, found: 315.1650; EIMS m/z 315 (M$^+$, 16), 300 (33), 224 (26), 73 (100).

Example 7c

Representative Procedure for Iododesilylation. 4-(1-Hydroxy-1-propyl)-6-iodo-2-methoxy-3-methylpyridine A sonicated solution of ICl (297 mg, 2.3 mmol) in CCl$_4$ (1.5 mL) at 0° C. was added to a solution of 4-(1-hydroxy-1-propyl)-2-methoxy-3-methyl-6-trimethylsilylpyridine (231 mg, 0.91 mmol) in CH$_2$C$_{12}$ (2 mL) at 0° C., and the mixture was stirred protected from light for 24 h. The solution was diluted with CH$_2$C$_{12}$ and washed with aqueous Na$_2$S$_2$O$_3$ and brine, dried (Na$_2$SO$_4$), evaporated and the residue purified by flash chromatography (hexanes-EtOAc 25:1) to afford unreacted silane (89 mg, 39%) and the iodide (135 mg, 48%) as a white solid, mp 57–58° C.: $^1$H NMR (300 MHz, CDCl$_3$) δ7.41 (s, 1H), 4.75 (t, J=6.4 Hz, 1H), 3.90 (s, 3H), 2.12 (br s, 1H), 2.03 (s, 3H), 1.64 (quint, J=7.3 Hz, 2H), 0.95 (t, J=7.3 Hz, 3H); $^{13}$C NMR (75 MHz, CDCl$_3$) δ161.6, 154.8, 124.7, 119.7, 116.2, 110.1, 70.8, 54.5, 30.6, 10.9, 10.2; HRMS (EI) m/z calcd for C$_{10}$H$_{14}$NO$_2$I (M$^+$): 307.0069, found: 307.0057; EIMS m/z 307 (M$^+$, 100), 278 (27), 151 (31).

1-(6-Iodo-2-methoxy-3-methylpyridin-4-yl)-2,2-dimethyl-propan-1-ol

White solid (56% iodide and 41% of recovered silane), flash chromatography (hexanes-EtOAc 25:1), mp 64–65° C.: $^1$H NMR (300 MHz, CDCl$_3$) δ7.37 (s, 1H), 4.62 (s, 1H), 3.89 (s, 3H), 2.23 (s, 1H), 2.03 (s, 3H), 0.90 (s, 9H); $^{13}$C NMR (75 MHz, CDCl$_3$) δ161.6, 152.6, 126.9, 118.1, 109.1, 75.7, 54.4, 37.0, 26.0, 12.5; HRMS (EI) m/z calcd for C$_{12}$H$_{18}$INO$_2$ (M$^+$) : 335.0375, found: 335.0382; EIMS m/z 335 (M$^+$, 25), 279 (100).

1-(6-Iodo-2-methoxy-3-methylpyridin-4-yl)-2-phenyl-ethanol

Pale yellow solid (49% iodide and 37% of recovered silane), flash chromatography (hexanes-EtOAc 25:1); mp 69–70° C.: $^1$H NMR (300 MHz, CDCl$_3$) δ7.50 (s, 1H), 7.35–7.25 (m, 3H), 7.21–7.18 (m, 2H), 4.98 (dd, J=8.8, 4.1 Hz, 1H), 3.93 (s, 3H), 2.92 (dd, J=13.8, 4.1 Hz, 1H), 2.78 (dd, J=13.8, 8.8 Hz, 1H), 2.22 (br s, 1H), 2.04 (s, 3H); $^{13}$C NMR (75 MHz, CDCl$_3$) δ1.7, 153.8, 137.3, 130.0, 128.9, 127.2, 124.6, 116.1, 110.3, 70.7, 54.5, 44.4, 10.8; HRMS (EI) m/z calcd for C$_{15}$H$_{16}$INO$_2$ (M$^+$) 369.0226, found: 369.0219; EIMS m/z 369 (M$^+$, 100), 277 (74).

Example 7d

General Procedure for Iodopyridone Formation 4-(1-Hydroxypropyl)-6-iodo-3-methyl-1H-pyridin-2-one To a solution of 4(1-hydroxy-1-propyl)-6-iodo-2-methoxy-3-methylpyridine (334 mg, 1.09 mmol) and NaI (262 mg, 1.75 mmol) in CH$_3$CN (3.5 mL) was added chlorotrimethylsilane (0.19 mg, 0.22 mL, 1.75 mmol) and H$_2$O (10 µL, 0.55 mmol) The mixture was heated at 65° C.

for 5 h protected from light. After cooling, it was washed with aqueous Na$_2$S$_2$O$_3$ and brine and extracted with EtOAc-MeOH, dried (MgSO$_4$) and evaporated and the residue subjected to flash chromatography (CH$_2$Cl$_2$-MeOH 9:1) affording the iodopyridone (261 mg, 82%) as a white solid, mp 174–175° C.: $^1$H NMR (300 MHz, CD$_3$OD) δ6.96 (s, 1H), 4.69 (t, J=6.5 Hz, 1H), 2.02 (s, 3H), 1.62 (quint, J=7.3 Hz, 2H), 0.96 (t, J=7.3 Hz, 3H); $^{13}$C NMR (75 MHz, CD$_3$OD) δ166.2, 157.3, 123.1, 118.9, 93.0, 71.5, 31.1, 11.5, 10.5; HRMS (EI) m/z calcd for C$_9$H$_{12}$NO$_2$I (M$^+$) : 292.9913, found: 292.9909; EIMS m/z 293 (M$^+$, 100), 275 (35), 148 (24).

4-(1-Hydroxy-2,2-dimethylpropyl)-6-iodo-3-methyl-1H-pyridin-2-one

Pale yellow solid (92%), flash chromatography (CH$_2$Cl$_2$-MeOH 9:1), mp 186–187° C.; $^1$H NMR (300 MHz, CD$_3$OD) δ6.91 (s, 1H), 4.55 (s, 1H), 2.02 (s, 3H), 0.91 (s, 9H); $^{13}$C NMR (75 MHz, CD$_3$OD) δ166.1, 155.2, 125.4, 121.2, 91.1, 76.5, 37.9, 26.8, 13.5; HRMS (EI) m/z calcd for C$_{11}$H$_{16}$INO$_2$ (M$^+$) 321.0226, found 321.0232; EIMS m/z 321 (M$^+$, 25), 238 (100).

4-(1-Hydroxy-2-phenyl-ethyl)-6-iodo-3-methyl-1H-pyridin-2-one

White solid (76%), flash chromatography (CH$_2$Cl$_2$-MeOH 9:1); mp. 166–167° C.: $^1$H NMR (300 MHz, CD$_3$OD) δ7.25–7.20 (m, 3H), 7.13–7.10 (m, 2H), 6.98 (s, 1H), 4.97 (dd, J=6.9, 6.7 Hz, 1H), 2.96 (dd, J=13.4, 6.9 Hz, 1H), 2.82 (dd, J=13.4, 6.7 Hz, 1H), 1.74 (s, 3H); $^{13}$C NMR (75 MHz, CD$_3$OD) δ166.1, 154.7, 137.3, 129.3, 127.8, 126.1, 122.3, 117.5, 70.0, 43.3, 9.8; HRMS (EI) m/z calcd for C$_{14}$H$_{14}$NO$_2$I (M$^+$): 355.0069, found: 355.0074; EIMS m/z 355 (M$^+$, 7), 301 (8), 197 (24), 91 (100).

Example 7e

Representative Procedure for N-Alkylation. 4-(1-Hydroxypropyl)-6-iodo-3-methyl-1-prop-2-ynyl-1H-pyridin-2-one (4b)

To a solution of 4-(1-hydroxypropyl)-6-iodo-3-methyl-1H-pyridin-2-one (200 mg, 0.69 mmol) in DME (2.4 mL) and DMF (0.6 mL) at 0° C. was added portionwise NaH (30 mg, 0.76 mmol, 60% in mineral oil). After 10 min, LiBr (120 mg, 1.38 mmol) was added and the cooling bath removed. Propargyl bromide (170 mg, 0.16 mL, 80% in toluene) was added 10 min later and the mixture was heated at 70° C. for 14 h protected from light. The reaction was cooled, diluted with EtOAc. This was washed with brine, dried (Na$_2$SO$_4$) and evaporated. The residue was purified by flash chromatography (CH$_2$Cl$_2$-EtOAc 9:1) to yield 4b (195 mg, 86%) as a pale yellow solid. mp 126–127° C.; $^1$H NMR (300 MHz, CDCl$_3$) δ7.05 (s, 1H), 5.01 (d, J=17.0, 1H), 4.92 (d, J=17.0, 1H), 4.68–4.64 (m, 1H), 2.39 (t, J=2.6 Hz, 1H) 1.94 (s, 3H), 1.58 (quint, J=7.3 Hz, 2H), 0.90 (t, J=7.3 Hz, 3H); $^{13}$C NMR (75 MHz, CDCl$_3$) δ162.6, 153.4, 124.2, 118.7, 94.7, 73.1, 70.6, 44.4, 30.0, 12.3, 10.2 (one signal is not observed); HRMS (EI) m/z calcd for C$_{12}$H$_{14}$NO$_2$I (M$^+$): 331.0069, found: 331.0067; EIMS m/z 331 (M$^+$, 100), 302 (20).

1-[3-(tert-Butyldimethylsilanyl)prop-2-ynyl]-4-(1-hydroxy-2-phenyl-ethyl)-6-iodo-3-methyl-1H-pyridin-2-one Pale yellow solid (79%), mp 98–99° C.: $^1$H NMR (300 MHz, CDCl$_3$) δ7.28–7.22 (m, 3H), 7.16–7.14 (m, 2H), 7.12 (s, 1H), 5.05 (br s, 2H), 4.93–4.85 (m, 1H), 3.17 (br s, 1H), 2.84 (br d, J=7.2 Hz, 2H0, 1.87 (s, 3H), 0.93 (s, 9H), 0.09 (s, 6H); $^{13}$C NMR (75 MHz, CDCl$_3$) δ162.3, 151.9, 137.1, 129.5, 128.6, 126.9, 124.1, 118.2, 99.8, 94.8, 88.6, 70.5, 60.5, 44.7, 43.5, 26.1, 21.1, 16.7, 14.3, 12.2, −4.7; HRMS (EI) m/z calcd for C$_{23}$H$_{30}$INO$_2$Si (M$^+$): 507.1091, found: 507.1099; EIMS m/z 507 (M$^+$, 14), 450 (100).

4-(1-Hydroxypropyl)-6-iodo-3-methyl-1-(3-phenylprop-2-ynyl)-1H-pyridin-2-one (4e)

White solid (69%), mp 156–157° C.: $^1$H NMR (300 MHz, CDCl$_3$) δ7.46–7.42 (m, 2H), 7.29–7.23 (m, 3H), 7.11 (s, 1H), 5.32 (d, J=17.0 Hz, 1H), 5.16 (d, J=17.0 Hz, 1H), 4.62 (t, J=6.5 Hz, 1H), 3.42 (br s, 1H), 1.89 (s, 3H), 1.65–1.53 (m, 2H), 0.83 (t, J=7.3 Hz, 3H); $^{13}$C NMR (75 MHz, CDCl$_3$) δ162.8, 153.5, 132.0, 128.8, 128.4, 124.3, 122.5, 118.9, 94.9, 84.7, 83.3, 70.4, 45.0, 30.0, 12.2, 10.0; HRMS (EI) m/z calcd for C$_{18}$H$_{18}$NO$_2$I (M$^+$) : 407.0382, found: 407.0400; EIMS m/z 407 (M$^+$, 40), 378 (7), 115 (100).

4-(1-Hydroxy-2,2-dimethyl-propyl)-6-iodo-3-methyl-1-prop-2-ynyl-1H-pyridin-2-one (4c)

Pale yellow solid (68%); mp 105–106° C.: $^1$H NMR (300 MHz, CDCl$_3$) δ7.07 (s, 1H), 5.14 (d system, J=17.0, 1H), 4.97 (d, J=17.0, 1H), 4.51 (s, 1H), 2.89 (s, 1H), 2.34 (t, J=2.1 Hz, 1H), 1.96 (s, 3H), 0.93 (s, 9H); $^{13}$C NMR (75 MHz, CDCl$_3$) δ162.5 151.3, 126.6, 120.8, 93.0, 75.7, 73.1, 44.3, 37.1, 26.2, 13.9.

4-(1-Hydroxy-2-phenylethyl)-6-iodo-3-methyl-1-prop-2-ynyl-1H-pyridin-2-one (4d)

Pale yellow solid (62%), mp 112–113° C.: $^1$H NMR (300 MHz, CDCl$_3$) δ7.32–7.27 (m, 3H), 7.23–7.17 (m, 2H), 7.15 (s, 1H), 5.06 (d, J=17.0, 1H), 4.99 (d, J=17.0, 1H), 4.91–4.88 (m, 1H), 2.98 (s, 1H), 2.83 (d, J=6.5 Hz, 2H), 2.27 (s, 1H), 1.86 (s, 3H); $^{13}$C NMR (75 MHz, CDCl$_3$) δ162.5 152.3, 137.2, 129.5, 128.7, 127.0, 124.3, 118.4, 94.8, 73.1, 70.5, 44.4, 43.5, 12.0.

Example 8

Diisopropyl-(3, 3, 4, 4, 5, 5, 6, 6, 6-nonafluorohexyl)silane

To a solution of 1, 1, 1, 2, 2, 3, 3, 4, 4-nonafluoro-6-iodo-hexane (1.0 g, 2.67 mmol) in Et$_2$O (10 mL) at −70° C. was added $^t$BuLi (4.0 mL, 2.1 equiv, 1.7 M in pentane). The bath temperature was raised to −40° C. over 30 min. It was then cooled again to −70° C. and chlorodiisopropylsilane (420 mg, 493 μL, 2.40 mmol) was added. The mixture was warmed to 23° C. and stirred for 12 h. Water was added and the mixture was extracted with Et$_2$O. The Et2O layer was dried (MgSO$_4$) and evaporated. The residue was purified by flash chromatography (hexanes) to give the fluorous silane (805 mg, 83%) as a colorless oil. $^1$H NMR (300 MHz, CDCl$_3$) δ3.50 (s, 1H), 2.24–2.01 (m, 2H), 1.09 (s, 12 H), 0.94–0.79 (s, 3H); $^{13}$C NMR (75 MHz, CDCl$_3$) δ123.2–110.8 (m, 4C), 27.1 (t, (J=23.2 Hz), 18.6 (d, J=26.0 Hz), 10.4, −2.2; $^{19}$F NMR (282.4 MHz, CDCl$_3$) δ−80.0 (3F), −115.6 (2F), −123.2 (2F), −125.02 (2F).

The Following Compounds Were Prepared by Similar Procedures (3, 3, 4, 4, 5, 5, 6, 6, 7, 7, 8, 8, 8-Tridecafluorooctyl)diisopropylsilane $^1$H NMR (300 MHz, CDCl$_3$) δ3.50 (s, 1H), 2.24–2.02 (m, 2H), 1.08 (s, 12 H), 0.91–0.82 (s, 3H); $^{13}$C NMR (75 MHz, CDCl$_3$) δ122.4–109.7 (m, 6C), 27.4 (t, J=23.3 Hz), 18.7 (d, J=25.8 Hz), 10.6, −1.9; $^{19}$F NMR (282.4 MHz, CDCl$_3$) δ−81.7 (3F), −117.0 (2F), −122.5 (2F), −123.4 (2F), −123.9 (2F), −126.7 (2F).

(3, 3, 4, 4, 5, 5, 6, 6, 7, 7, 8, 8, 9, 9, 10, 10, 10-Heptadecafluorodecyl)-diisopropylsilane $^1$H NMR (300 MHz, CDCl$_3$) δ3.49 (s, 1H), 2.21–2.09 (m, 2H), 1.05 (s, 12 H), 0.87–0.83 (s, 3H); $^{13}$C NMR (75 MHz, CDCl$_3$) δ121.8–107.4 (m, 8C), 27.4 (t, J=23.4 Hz), 18.8 (d, J=25.9 Hz), 10.6, −1.9; $^{19}$F NMR (282.4 MHz, CDCl$_3$) δ−80.9 (3F), −117.9 (2F), −122.4 (6F), −123.4 (2F), −123.8 (2F), −126.6 (2F).

(3, 3, 4, 4, 5, 5, 6, 6, 7, 7, 8, 8, 9, 9, 10, 10, 11, 11, 12, 12, 12-Heneicosafluorododecyl)-diisopropylsilane $^1$H NMR (300 MHz, CDCl$_3$) δ3.50 (s, 1H), 2.18–2.09 (m, 2H), 1.06 (s, 12 H), 0.86–0.82 (s, 3H); $^{13}$C NMR (75 MHz, CDCl$_3$) δ121.7–108.5 (m, 10C), 27.4 (t, J=23.0 Hz), 18.8 (d, J=25.9 Hz), 10.6, −1.9; $^{19}$F NMR (282.4 MHz, CDCl$_3$) δ−81.3 (3F), −117.0 (2F), −122.3 (8F), −123.4 (2F), −124.8 (2F), −127.4 (2F).

Example 9a

1-[3-(tert-Butyldimethylsilanyl)-prop-2-ynyl]-4-[1-(dimethyloctylsilanyloxy)-2-phenylethyl]-6-iodo-3-methyl-1H-pyridin-2-one (5a)

To a solution of 1-[3-(tert-butyldimethylsilanyl)prop-2-ynyl]-4-(1-hydroxy-2-phenylethyl)-6-iodo-3-methyl-1H-pyridin-2-one 4a (60 mg, 0.12 mmol) and 4-dimethylaminopyridine (2 mg, 1.2 μmol) in CH$_2$Cl$_2$ (2 mL) was added NEt$_3$ (49 mg, 66 μL, 0.48 mmol) and chlorodimethyloctylsilane (62 mg, 77 μL, 0.3 mmol). The resulting mixture was stirred for 12 h. The solvent was evaporated and the residue was purified by flash chromatography (hexanes-EtOAc 15:1) to afford 5a (41 mg, 51%) as a yellow oil. $^1$H NMR (300 MHz, CDCl$_3$) δ7.32–7.24 (m, 3H), 7.15–7.12 (m, 2H), 7.08 (s, 1H), 5.14 (d, J=17.0, 1H), 5.09 (d, J=17.0, 1H), 4.79 (t, J=6.4 Hz, 1H), 2.79 (d, J=6.4 Hz, 2H), 1.98 (s, 3H), 1.39–1.11 (m, 14H), 0.94 (s, 9H), 0.90–0.87 (m, 3H), 0.10 (s, 6H), −0.17 (s, 3H), −0.18 (s, 3H); $^{13}$C NMR (75 MHz, CDCl$_3$) δ162.3, 152.0, 137.8, 129.7, 129.1, 128.3, 127.5, 127.2, 126.6, 118.6, 88.4, 44.6, 33.5, 32.0, 29.4, 29.3, 26.1, 23.2, 23.0, 22.7, 17.9, 16.5, 14.2, 12.0, −0.19, −2.05, −4.78.

Example 9b

4-{1-[Diisopropyl-(3, 3, 4, 4, 5, 5, 6, 6, 6-nonafluorohexyl)silanyloxy]propyl}-6-iodo-3-methyl-1-prop-2-ynyl-1H-pyridin-2-one (5b)

To a solution of 4-(1-hydroxypropyl)-6-iodo-3-methyl-1-prop-2-ynyl-1H-pyridin-2-one 4b (44 mg, 0.13 mmol) and 4-dimethylaminopyridine (2 mg, 1.2 μmol) in CH$_2$Cl$_2$ (2 mL) was added NEt$_3$ (53 mg, 74 μL, 0.52 mmol) and bromodiisopropyl(3, 3, 4, 4, 5, 5, 6, 6, 6-nonafluorohexyl)silane (147 mg, 0.33 mmol, prepared by mixing diisopropyl-(3, 3, 4, 4, 5, 5, 6, 6, 6-nonafluorohexyl)silane and Br$_2$) and the mixture was stirred for 12 h. The solvent was evaporated and the residue was purified by flash chromatography (hexanes-EtOAc 15:1) to afford 5b (75 mg, 82%) as a colorless oil: $^1$H NMR (300 MHz, CDCl$_3$) δ6.99 (s, 1H), 5.12 (d, J=16.5, 1H), 5.00 (d, J=16.5, 1H), 4.75 (t, J=6.0 Hz, 1H), 2.33–2.31 (m, 1H), 2.07–1.99 (m, 2H) 2.06 (s, 3H), 1.84–1.60 (m, 2H), 1.00 (s, 14H), 0.88 (t, J=7.4 Hz, 3H), 0.83–0.79 (m, 2H); $^{13}$C NMR (75 MHz, CDCl$_3$) δ162.4, 152.5, 123.7, 118.6, 94.2, 72.8, 71.5, 44.3, 31.1, 25.3, 17.5, 12.6, 9.4, 0.3.

Example 9c

4-{1-[Diisopropyl-(3, 3, 4, 4, 5, 5, 6, 6, 7, 7, 8, 8, 8-tridecafluorooctyl)-silanyloxy]-2,2-dimethyl-propyl}-6-iodo-3-methyl-1-prop-2-ynyl-1H-pyridin-2-one (5c)

To a solution of 4-(1-hydroxy-2,2-dimethylpropyl)-6-iodo-3-methyl-1-prop-2-ynyl-1H-pyridin-2-one 4c (31 mg, 0.09 mmol) in CH$_2$Cl$_2$ (2 mL) was added 2,6-lutidine (37 mg, 40 μL, 0.36 mmol) and (3, 3, 4, 4, 5, 5, 6, 6, 7, 7, 8, 8, 8-tridecafluorooctyl)diisopropyl silyl trifluoromethanesulfonate (158 mg, 0.27 mmol, prepared by mixing (3, 3, 4, 4, 5, 5, 6, 6, 7, 7, 8, 8, 8-tridecafluorooctyl)diisopropyl silane and TfOH at 0° C. and stirring for 12 h) and the mixture was stirred for 12 h. The solvent was evaporated and the residue was purified by flash chromatography (hexanes-EtOAc 15:1) to afford 5c (36 mg, 49%) as a colorless oil: $^1$H NMR (300 MHz, CDCl$_3$) δ6.97 (s, 1H), 5.10 (d, J=17.0, 1H), 5.01 (part B of AB system, J=17.0, 1H), 4.60 (s, 1H), 2.33–2.31 (m, 1H), 2.12–1.91 (m, 2H), 2.09 (s, 3H), 1.08 (s, 9H), 0.90 (s, 14H), 0.64–0.57 (m, 2H); $^{13}$C NMR (75 MHz, CDCl$_3$) δ162.2, 150.6, 126.2, 120.6, 93.0, 72.8, 44.2, 38.0, 26.3, 25.1, 17.6, 14.1, 12.8, 0.6.

Example 9d

4-{1-[(3, 3, 4, 4, 5, 5, 6, 6, 7, 7, 8, 8, 9, 9, 10, 10, 10-Heptadecafluorodecyl)diisopropylsilanyloxy]-2-phenyl-ethyl}-6-iodo-3-methyl-1-prop-2-ynyl-1H-pyridin-2-one (5d)

To a solution of 4-(1-hydroxy-2-phenyl-ethyl)-6-iodo-3-methyl-1-prop-2-ynyl-1H-pyridin-2-one 4d (65 mg, 0.17 mmol) in CH$_2$Cl$_2$ (2 mL) was added 4-dimethyaminopyridine (2 mg, 17 μmol), NEt$_3$ (70 mg, 96 μL, 0.68 mmol), and bromo-(3, 3, 4, 4, 5, 5, 6, 6, 7, 7, 8, 8, 9, 9, 10, 10, 10-heptadecafluorodecyl)diisopropylsilane (277 mg, 0.43 mmol, prepared by mixing (3, 3, 4, 4, 5, 5, 6, 6, 7, 7, 8, 8, 9, 9, 10, 10, 10-heptadecafluorodecyl)diisopropylsilane and Br$_2$) and the mixture was stirred for 12 h. The solvent was evaporated and the residue was purified by flash chromatography (hexanes-EtOAc 15:1) to afford 5d (116 mg, 70%) as a colorless oil: $^1$H NMR (300 MHz, CDCl$_3$) δ7.27–7.22 (m, 3H), 7.12–7.10 (m, 2H), 7.02 (s, 1H), 5.10 (d, J=16.5, 1H), 5.01 (d, J=16.5, 1H), 4.93 (t, J=6.5 Hz, 1H), 2.84–2.82 (m, 2H), 2.33–2.32 (m, 1H), 1.93–1.83 (m, 2H), 1.93 (s, 3H), 0.90 (s, 14H), 0.64–0.57 (m, 2H); $^{13}$C NMR (75 MHz, CDCl$_3$) δ162.2, 152.0, 136.9, 129.7, 128.5, 127.0, 123.7, 118.3, 114.8, 94.4, 72.8, 72.2, 44.9, 44.3, 25.1, 17.4, 12.5, 11.9, 0.1.

Example 9e

4-{1-[(3, 3, 4, 4, 5, 5, 6, 6, 7, 7, 8, 8, 9, 9, 10, 10, 11, 11, 12, 12, 12-Heneicosafluorododecyl)diisopropylsilanyloxy]propyl}-6-iodo-3-methyl-1-(3-phenylprop-2-ynyl)-1H-pyridin-2-one (5e)

To a solution of 4-(1-hydroxypropyl)-6-iodo-3-methyl-1-(3-phenylprop-2-ynyl)-1H-pyridin-2-one 4e (100 mg, 0.25 mmol) in CH$_2$C$_{12}$ (3 mL) was added 4-dimethyaminopyridine (3 mg, 25 μmol), NEt$_3$ (76 mg, 105 μL, 0.75 mmol) and bromo-(3, 3, 4, 4, 5, 5, 6, 6, 7, 7, 8, 8, 9, 9, 10, 10, 11, 11, 12, 12, 12-heneicosafluorododecyl) diisopropylsilane (365 mg, 0.50 mmol, prepared by mixing (3, 3, 4, 4, 5, 5, 6, 6, 7, 7, 8, 8, 9, 9, 10, 10, 11, 11, 12, 12, 12-heneicosafluorododecyl)diisopropylsilane and $Br_2$) and the mixture was stirred for 12 h. The solvent was evaporated and the residue was purified by flash chromatography (hexanes -EtOAc 15:1) to afford 5e (118 mg, 75%) as a colorless oil: $^1$H NMR (300 MHz, $CDCl_3$) δ7.47–7.45 (m, 2H), 7.30–7.27 (m, 2H), 7.04 (s, 1H), 5.42 (d, J=17.1, 1H), 5.19 (d, J=17.1, 1H), 4.77 (t, J=6.0 Hz, 1H), 2.23–2.03 (m, 2H), 2.08 (s, 3H), 1.70–1.62 (m, 2H), 1.02 (s, 14H), 0.90 (t, J=7.4 Hz, 3H), 0.88–0.82 (m, 2H); $^{13}$C NMR (75 MHz, $CDCl_3$) δ162.5, 152.5, 132.0, 128.6, 128.2, 123.6, 122.6, 118.7, 94.4, 84.5, 83.3, 71.6, 44.8, 31.1, 25.3, 17.4, 12.5, 9.5, 0.3.

Example 10

General Procedure for the Radical Cyclization to Make Authentic Samples

A mixture of N-alkylated pyridone 5 g and 4-methylphenyl isonitrile (3 equiv, 1M in benzene) and hexamethylditin (1.5 equiv) was irradiated with a 275W GE sunlamp for 5 h. After cooling, the solvent was evaporated and the residue was purified by flash chromatography (gradient $CH_2Cl_2 \rightarrow CH_2Cl_2$-EtOAc 50:1) to yield the corresponding silyl mappicine 6.

Example 10a 12-(tert-Butyldimethylsilanyl)-7-[1 (dimethylnonylsilanyloxy)-2-phenyl-ethyl]-2,8-dimethyl-11H-indolizino[1,2-b]quinolin-9-one (6a)

Pale yellow solid (45%): $^1$H NMR (300 MHz, $CDCl_3$) δ8.15 (d, J=8.6, 1H), 8.01 (s, 1H), 7.66 (s, 1H), 7.60 (d, J=8.6 Hz, 1H), 7.31–7.16 (m, 5H), 5.29 (s, 2H), 5.01–4.99 (m, 1H), 2.94–2.88 (m, 2H), 2.59 (s, 3H), 2.34–2.32 (m, 1H), 2.06 (s, 3H), 1.26–1.15 (m, 12H), 1.01 (s, 9H), 0.85–0.81 (m, 3H), 0.70 (s, 6H), 0.41–0.37 (m, 2H), −0.16 (s, 6H); MS m/z 668 ($M^+$, 5), 575 (12), 496 (83), 405 (100).

Example 10b

7-{1-[Diisopropyl-(3, 3, 4, 4, 5, 5, 6, 6, 6-nonafluorohexyl)silanyloxy]propyl}-2,8-dimethyl-11H -indolizino[1,2-b]quinolin-9-one (6b)

Pale yellow solid (67%): $^1$H NMR (300 MHz, $CDCl_3$) δ8.23 (s, 1H), 8.10 (d, J=8.4 Hz, 1H), 7.66–7.61 (m, 2H), 7.49 (s, 1H), 5.24 (s, 2H), 4.99 (t, J=6.3 Hz, 1H), 2.59 (s, 3H), 2.28 (s, 3H), 2.21–2.05 (m, 2H), 1.83–1.77 (m, 2H), 1.06 (s, 14H), 0.93 (t, J=7.4 Hz, 3H), 0.89–0.82 (m, 2H); MS m/z 660 ($M^+$, 36), 409 (43), 303 (100).

Example 10c

7-{1-[Diisopropyl-(3, 3, 4, 4, 5, 5, 6, 6, 7, 7, 8, 8, 8-tridecafluorooctyl)silanyloxy]-2,2-dimethylpropyl}-2,8-dimethyl-11H-indolizino[1,2-b] quinolin-9-one (6c)

Pale yellow solid (30%): $^1$H NMR (300 MHz, $CDCl_3$) δ8.22 (s, 1H), 8.14 (d, J=8.6 Hz, 1H), 7.65–7.60 (m, 2H), 7.49 (s, 1H), 5.24 (s, 2H), 4.99 (s, 1H), 2.58 (s, 3H), 2.33 (s, 3H), 2.05–1.97 (m, 2H), 1.06 (s, 9H), 1.01 (s, 14H), 0.84–0.75 (m, 2H); MS m/z 808 ($M^+$, 16), 752 (16), 205 (100).

Example 10d

7-{1-[(3, 3, 4, 4, 5, 5, 6, 6, 7, 7, 8, 8, 9, 9, 10, 10, 10-Heptadecafluorodecyl)diisopropylsilanyloxy]-2-phenylethyl}-2,8-dimethyl-11H-indolizino[1,2-b] quinolin-9-one (6d)

Pale yellow solid (64%) $^1$H NMR (300 MHz, $CDCl_3$) δ8.25 (s, 1H), 8.15 (d, J=8.6 Hz, 1H), 7.67–7.62 (m, 3H), 7.25–7.15 (s, 5H), 5.25 (s, 2H), 5.17–5.15 (m, 1H), 3.03–2.96 (m, 2H), 2.60 (s, 3H), 2.07 (s, 3H), 2.05–1.86 (m, 2H), 1.01 (s, 14H), 0.66–0.61 (m, 2H); MS m/z 942 ($M^+$, 23), 851 (27), 205 (100).

Example 10e

7-{1-[(3, 3, 4, 4, 5, 5, 6, 6, 7, 7, 8, 8, 9, 9, 10, 10, 11, 11, 12, 12, 12-Heneicosafluorododecyl) diisopropylsilanyloxy]propyl}-2,8-dimethyl-12-phenyl-11H-indolizino[1,2-b]quinolin-9-one (6e)

Pale yellow solid (46%) :$^1$H NMR (300 MHz, $CDCl_3$) δ8.17 (d, J=8.6 Hz, 1H), 7.63–7.59 (m, 4H), 7.54 (s, 1H), 7.44–7.42 (m, 2H), 5.05 (s, 2H), 4.99 (t, J=6.1 Hz, 1H), 2.47 (s, 3H), 2.26 (s, 3H), 2.13–2.05 (m, 2H), 1.87–1.78 (m, 2H) 1.06 (s, 14H), 0.94 (t, J=7.4 Hz, 3H), 0.87–0.82 (m, 2H); MS m/z 1056 ($M^+$, 37), 485 (37), 379 (100).

Example 11

Synthesis and Separation of a Representative Mixture Library

A mixture of 5a (4.8 mg, 7.0 μmol), 5b (4.9 mg, 7.1 μmol), 5c (5.2 mg, 6.3 μmol), 5d (6.3 mg, 6.6 μmol), 5e (7.0 mg, 6.8 μmol) and 4-methylphenyl isonitrile (3 equiv 1M in benzene) and hexamethylditin (1.5 equiv) was irradiated with a 275W GE sunlamp for 5 h. After cooling, the solvent was evaporated and the residue purified by flash chromatography ($CH_2Cl_2$, then $CH_2Cl_2$-EtOAc 50:1) to yield the silyl mappicine mixture. This was separated by preparative HPLC with a Fluofix™ column using the following step gradient: MeOH:$H_2O$ 80:20, 0–5 min, MeOH:$H_2O$ 90:10, 5–25 min; MeOH, >25 min. Isolated yields of silyl mappicines are listed in order of elution: 6a (1.6 mg, 36%), 6b (2.0 mg, 41%), 6c (1.5 mg, 29%), 6d (2.2 mg, 36%), 6e (3.0 mg, 43%). These products were identical to the authentic samples prepared in Example 10.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. A method of separating compounds, the method comprising the steps of:
   a. tagging at least a first organic compound with a first tagging moiety to result in a first tagged compound;
   b. tagging at least a second organic compound with a second tagging moiety different from the first tagging moiety to result in a second tagged compound; and
   c. physically separating the first tagged compound from a mixture including at least the second tagged compound using a separation technique based upon differences between the first tagging moiety and the second tagging moiety, the separation technique being based upon difference in fluorous nature of the first tagged compound and the second tagged compound.

2. The method of claim 1 wherein the first tagging moiety and the second tagging moiety are fluorous moieties that differ in fluorous content or structure.

3. The method of claim 2 wherein the first tagged compound and the second tagged compound are physically separated using fluorous reverse phase chromatography.

4. The method of claim 1 wherein the first tagging moiety and the second tagging moiety are selected so that the order in which the first tagged compound and the second tagged compound physically separate is predetermined.

5. A method of physically separating compounds, the method comprising the steps of:
   a. tagging at least a first organic compound with a first fluorous tagging moiety to result in a first tagged compound;
   b. tagging at least a second organic compound with a second fluorous tagging moiety different from the first tagging moiety to result in a second tagged compound; and
   c. physically separating the first tagged compound from a mixture including the second tagged compound using a separation technique based upon differences in the fluorous nature of the first tagged compound and the second tagged compound.

6. The method of claim 5 wherein the first fluorous tagging moiety and the second fluorous tagging moiety differ in fluorine content or structure.

7. The method of claim 6 wherein the first tagged compound and the second tagged compound are physically separated using fluorous reverse phase chromatography.

8. A method of physically separating compounds, the method comprising the steps of: tagging a plurality of organic compounds with a plurality of fluorous tagging moieties to result in a plurality of tagged compounds, each of the fluorous tagging moieties being different; and physically separating at least one of the plurality of tagged compounds from other tagged compounds with a different tag using a separation technique based upon differences in the fluorous nature of the tagged compounds.

9. The method of claim 8 wherein a first fluorous tagging moiety and a second fluorous tagging moiety of the plurality of fluorous tagging moieties differ in fluorine content or structure.

10. The method of claim 9 wherein a first tagged compound tagged with the first fluorous tagging moiety and a second tagged compound tagged with the second fluorous tagging moiety are physically separated using fluorous reverse phase chromatography.

11. A method of preparation for a fluorous separation from a mixture of compounds, the method comprising the steps of:
   a. tagging a first organic compound with a first fluorous tagging moiety to result in a first fluorous tagged compound; and
   b. tagging at least a second organic compound with a second fluorous tagging moiety different from the first fluorous tagging moiety to result in a second fluorous tagged compound, the second fluorous tagging moiety being different from the first fluorous tagging moiety so that the first fluorous tagged compound can be physically separated from the second fluorous tagged compound in the mixture of compounds including the first fluorous tagged compound and the second tagged fluorous compound using a separation technique based upon the differences in the fluorous nature of the first fluorous tagged compound and the second fluorous tagged compound.

* * * * *